US007056503B2

(12) United States Patent
Rees et al.

(10) Patent No.: US 7,056,503 B2
(45) Date of Patent: Jun. 6, 2006

(54) ENCLOSURES HOUSING CELL-COATED SUPPORTS FOR TREATING TUMORS

(75) Inventors: Riley Rees, Ann Arbor, MI (US);
Jiyoun Kim, Ann Arbor, MI (US);
Daniel Remick, Ann Arbor, MI (US);
Belinda Adamson, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 209 days.

(21) Appl. No.: 09/962,059

(22) Filed: Sep. 25, 2001

(65) Prior Publication Data

US 2003/0007955 A1 Jan. 9, 2003

Related U.S. Application Data

(63) Continuation-in-part of application No. 09/640,990, filed on Aug. 18, 2000, now abandoned.

(60) Provisional application No. 60/149,744, filed on Aug. 19, 1999.

(51) Int. Cl.
*A61K 48/00* (2006.01)
*A61K 9/70* (2006.01)
*C12N 15/63* (2006.01)
*C12N 15/00* (2006.01)
*C12N 5/00* (2006.01)

(52) U.S. Cl. .................. 424/93.21; 424/93.7; 424/443; 424/489; 435/320.1; 435/325; 435/455

(58) Field of Classification Search .............. 424/93.7, 424/93.1, 93.2, 443, 489, 490; 435/320.1, 435/325, 455
See application file for complete search history.

(56) References Cited

U.S. PATENT DOCUMENTS

| | | | |
|---|---|---|---|
| 4,576,715 A | 3/1986 | Michaels et al. | 210/347 |
| 4,763,659 A | 8/1988 | Dunseath, Jr. | 128/640 |
| 4,997,443 A | 3/1991 | Walthall et al. | 210/232 |
| 5,152,757 A | 10/1992 | Eriksson | 604/305 |
| 5,269,917 A | 12/1993 | Stankowski | 210/232 |
| 5,294,446 A | 3/1994 | Schlameus et al. | 424/489 |
| 5,459,069 A | 10/1995 | Palsson et al. | 435/289.1 |
| 5,487,889 A | 1/1996 | Eckert et al. | 424/93.1 |
| 5,512,474 A | 4/1996 | Clapper et al. | 435/182 |
| 5,529,914 A | 6/1996 | Hubbell et al. | 435/182 |
| 5,545,423 A | 8/1996 | Soon-Shiong et al. | 424/484 |
| 5,563,068 A | 10/1996 | Zhang et al. | 435/295.2 |
| 5,643,773 A | 7/1997 | Aebischer et al. | 435/182 |
| 5,693,332 A | 12/1997 | Hansbrough | 424/426 |
| 5,712,163 A | 1/1998 | Parenteau et al. | 435/405 |
| 5,741,685 A | 4/1998 | Vacanti | 435/182 |
| 5,830,507 A | 11/1998 | Armstrong | 424/489 |
| 5,836,989 A | 11/1998 | Shelton | 607/27 |
| 5,972,332 A * | 10/1999 | Rees et al. | 424/93.7 |
| 6,070,103 A | 5/2000 | Ogden | 607/60 |
| 6,150,104 A | 11/2000 | Splawski et al. | 435/6 |
| 6,210,884 B1 | 4/2001 | Lizardi | 435/6 |

FOREIGN PATENT DOCUMENTS

WO WO 88/03785 2/1988

OTHER PUBLICATIONS

Merrick et al. (1996) Cell Growth & Diff., vol. 7(12), 1661-1669.*
U.S. Patent 5,714,170 (Baserga).
Sasaki et al., In Vivo 2000 Jul.-Aug.;14(4):535-41.
Nishizaki et al., Clinical Cancer Research, 5(5):1015-1023, 1999.
Lovik et al., J. Immunol. Meth., 179(1):59-69, 1995.
Kannon and Garrett, Dermatol. Surg., 21: 583-590 (1995).
Davies, Burns, 10: 94 (1983).
Myers et al. Am. J. Surgery, 170: 75-83 (1995).
Goeddel, Gene Therapy Expression Technology: Methods in Enzymology 185, Academic Press, San Diego, CA (1990).
Boyce et al., Surgery, 110: 866-76 (1991).
Barbul et al., Surgery, 105: 764-69 (1989).
Hansbrough et al., J. Burn Care Rehabil., 14: 485-94 (1993).
Gilchrest et al. Cell Bio Int. Rep. 4: 1009 (1980).
Schafer et al. Exp. Cell. Res. 183: 112 (1989).
Cook and Buskirk In Vitro Cell Dev. Biol. 31: 132 (1995).
Hansbrough et al., J. Am. Med. Assoc. 262: 2125 (1989).
Cooper et al., J. Surg. Res., 48: 528 (1990).
Ronfard et al. Burns, 17: 181 (1991).
Tinois et al., Exp. Cell Res., 193: 310 (1991).
Nanchahal and Ward, Brit. J. Plas. Surg. 45: 354 (1992).
Van der Merve et al., Burns, 16: 193 (1990).
Shi, Clinical Chemistry, 47:2, 164-172 [2001].
Boyce and Ham "Normal human epidermal keratinocytes," In *In Vitro Models for Cancer Research* (Weber and Sekely, eds.) CRC Press, Boca Raton, FL, pp. 245-274 (1985).
Schwarz et al., Wound Repair and Regeneration 3:204-212 (1995).
Yao et al., Hum Gene Ther. Feb. 10, 1999;10(3):419-27.
Yao et al., Hum Gene Ther. Sep. 1, 1998;9(13):1939-50.
T.K. Hunt and W.H. Goodson III, "Wound Healing," *Current Surgical Diagnosis & Treatment* (Way; Appleton & Lange), pp. 86-98 (1988).

(Continued)

*Primary Examiner*—Anne M. Wehbé
(74) *Attorney, Agent, or Firm*—Medlen & Carroll, LLP

(57) ABSTRACT

The present invention relates to devices, systems and methods for treating tumors. In particular, the present invention relates to enclosures housing cell-coated supports for promoting regression of tumors, such as cancerous tumors, papillomas, and warts. In preferred embodiments, the present invention provides methods of promoting tumor regression employing enclosures secreting therapeutic proteins.

20 Claims, 2 Drawing Sheets

OTHER PUBLICATIONS

Richey et al., "Topical Growth Factors and Wound Contraction in the Rat: Part I. Literature Review and Definition of the Rat Model," Ann. of Plastic Surgery 23(2):159-165 (1989).

G.D. Winter, "Formation of the Scab and the Rate of Epithelization of Superficial Wounds in the Skin of the Young Domestic Pig," *Nature*, 193:293-94 (1962).

Riley, "Wound Healing," *Am. Fam. Physician*, 24:107-113 (1981).

Pharmacia Catalog, pp. 26-27.

ICN Catalog,ICN Biomedical Research Products, pp. 130-131.

Sigma Catalog, pp. 144-145.

N. Carver et al., "The effect of backing materials on keratinocyte autograft take," Brit. J. of Plastic Surgery, 46:228-234 (1993).

J.F. Woessner, Jr., "Matrix metalloproteinases and their inhibitors in connective tissue remodeling," *FASEB J.*, 5:2145-2154 (1991).

Green et al., "Growth of Cultured human epidermal cells into multiple epithelia suitable for grafting," *Proc. Nat. Acad. Sci.* 76: 5665-5668 (1979).

Leigh et al., "Treatment of chronic venous ulcers with sheets of cultured allogenic keratinocyted," *Brit. J. Derm.* 117:591-597 (1987).

Takashima et al., "Activation of Rabbit Keratinocyte Fibronectin Receptor Function In Vivo During Wound Healing," *J. Invest. Derm.* 86:585-590 (1986).

Brown et al., "Enhancement of Epidermal Regeneration by Biosynthetic Epidermal Growth Factor," *J. Exp. Med.* 163:1319-1324 (1986).

Stompro, "Attachment of Growth Factors to Implantable Collagen," *Current Surgery* 47:35-37 (1990).

Jones et al., "Current Research Review: Effect of Topical Recombinant TFGβ on Healing of Partial Thickness Injuries," *J. Surg. Res.* 51:344-352 (1991).

Schultz et al., "EGF and TGF-α in Wound Healing and Repair," *J. Cell. Biochem.* 45:346-352 (1991).

Ejim et al., "Production of artificial-orientated mats and strands from plasma fibronectin: a morphological study," *Biomaterials* 14(10):743-748 (1993).

He and McCulley, "Growing human corneal epithelium on collagen sheild and subsequent transfer to denuded cornea in vitro," *Curr. Eye Res.* 10(9):851-863 (1991).

* cited by examiner

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
atggcacctg tacgatcact                                           20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
ttcagcacag gactctctgg                                           20

ENCLOSURES HOUSING CELL-COATED SUPPORTS FOR TREATING TUMORS

The present application is a Continuation-in-part of U.S. application Ser. No. 09/640,990, filed Aug. 18, 2000, now abandoned which claims priority to U.S. Provisional Application No. 60/149,744, filed Aug. 19, 1999, the contents of which are both hereby incorporated by reference.

The present application was funded in part with government support under NIH grant numbers FM 44918 and GM 50401. The government has certain rights in this invention.

FIELD OF THE INVENTION

The present invention relates to devices, systems, kits and methods for treating tumors. In particular, the present invention relates to enclosures housing cell-coated supports for promoting regression of tumors, such as cancerous tumors, neoplasms, papillomas, and warts.

BACKGROUND OF THE INVENTION

Each year, about one million people in the United States are diagnosed with skin cancer. Skin cancer is the most common type of cancer in the United States. According to recent estimates, 40 to 50 percent of Americans who live to age 65 will have skin cancer at least once.

The two most common kinds of skin cancer are basal cell carcinoma and squamous cell carcinoma. Basal cell carcinoma accounts for more than 90 percent of all skin cancers in the United States. Basal cell carcinoma is a slow-growing cancer that seldom spreads to other parts of the body. Squamous cell carcinoma also rarely spreads, but it does so more often than basal cell carcinoma. However, it is important that skin cancers be found and treated early because they can invade and destroy nearby tissue. Basal cell carcinoma and squamous cell carcinoma are known as nonmelanoma skin cancer.

Another type of cancer that occurs in the skin is melanoma, which begins in the melanocytes. The American Cancer Society reports that melanoma accounts for only 4 percent of skin cancer cases, but causes about 79% of skin cancer deaths. The American Cancer Society predicts that 16 percent of the newly diagnosed cases in the year 2000 will result in death.

Medical evidence indicates that the cytokine IL-1 inhibits tumor growth. However, systemic administration is very toxic to the human body. Therefore, what is needed are methods and devices for delivering tumor inhibiting compounds without systemic toxicity.

SUMMARY OF THE INVENTION

The present invention provides devices, kits, systems and methods for treating tumors. In particular, the present invention provides enclosures housing cell-coated supports (e.g., populated with cells) for promoting regression of tumors, such as cancerous tumors, papillomas, and warts.

In certain embodiments, the present invention provides methods for promoting tumor regression, comprising; a) providing; i) viable cells on a solid support, wherein the viable cells secrete at least one therapeutic protein, ii) an enclosure housing the solid support, wherein the enclosure comprises a material comprising pores, and iii) a subject with a tumor, and b) positioning the enclosure on the tumor of the subject such that regression of the tumor is promoted. In some embodiments, the present invention provides methods for promoting tumor regression, comprising; a) providing; i) viable cells on a solid support, wherein the viable cells secrete at least one therapeutic protein, ii) an enclosure housing the solid support, wherein the enclosure comprises mesh material, and iii) a subject with a tumor, and b) positioning the enclosure on the tumor of the subject such that regression of the tumor is promoted. In certain embodiments, the method further comprises performing a tumor susceptibility assay (e.g. before positioning the enclosure on the tumor). In particular embodiments, method further comprises performing a cell viability assay. In certain embodiments, the enclosure functions as the solid support (e.g. the cells are on the inside of the enclosure, instead of being on a separate solid support).

In some embodiments, the present invention provides methods for promoting tumor regression, comprising; a) providing; i) viable cells on a first solid support, wherein the viable cells secrete (or may be induced to secrete) at least one therapeutic protein, ii) a second solid support (e.g. sticky dressing), and iii) a subject with at least one tumor, and b) adhering the first solid support to the second solid support, and c) positioning the second solid support on the tumor of the subject such that regression of the tumor is promoted.

In certain embodiments, the present invention provides methods for promoting tumor regression, comprising; a) providing; i) viable cells on a solid support, wherein the viable cells secrete (or may be induced to secrete) at least one therapeutic protein, ii) an enclosure housing the solid support, wherein the enclosure comprises mesh material, and iii) a subject with at least one skin cancer tumor (e.g. melanoma, sarcoma, or carcinoma), and b) positioning the enclosure on the skin cancer tumor of the subject such that regression of the tumor is promoted. In particular embodiments, the skin cancer tumor is a head melanoma or neck melanoma. In some embodiments, the positioning comprises topical application of the enclosure to the skin cancer related tumor. In other embodiments, the positioning step causes the therapeutic protein to contact the tumor. In certain embodiments, the method further comprises performing a tumor susceptibility assay (e.g. before positioning the enclosure on the tumor). In particular embodiments, method further comprises performing a cell viability assay.

In certain embodiments, the present invention provides methods for producing a cell-containing enclosure for promoting tumor regression, comprising; a) providing, i) viable cells on solid support material, ii) a nucleic acid sequence encoding at least one therapeutic protein, wherein the therapeutic protein promotes tumor regression, and iii) an enclosure configured for housing the solid support material, wherein the enclosure comprises mesh material; and b) transfecting the viable cells on the solid support material with the nucleic acid sequence under conditions such that transfected cells are generated that secrete said therapeutic protein, and c) placing the solid support material into the enclosure to produce a cell-containing enclosure configured for promoting tumor regression (e.g. when placed on a tumor, such as a skin cancer tumor). In some embodiments, the transfection step employs liposomes. In preferred embodiments, the present invention provides cell-containing enclosures configured for promoting tumor regression that are produced by the methods of the present invention. In certain embodiments, the cells are tranfected prior to being seeded on the solid support material. In other embodiments, the therapeutic protein promotes wound healing, and the enclosure produced is configured for promoting wound healing.

In other embodiments, the present invention provides methods for producing a cell-containing enclosure for promoting tumor regression, comprising; a) providing, i) solid support material, ii) a culture medium comprising viable cells, iii) a vector comprising a nucleic acid sequence encoding a therapeutic protein, wherein the therapeutic protein promotes tumor regression, and iv) an enclosure configured for housing the solid support material, wherein the enclosure comprises mesh material, b) immersing the solid support in the culture medium under conditions such that viable cells migrate onto the solid support material, c) transfecting the viable cells with the vector, and d) introducing the solid support material into the enclosure to produce a cell-containing enclosure configured for promoting tumor regression (e.g. when placed on a tumor). In preferred embodiments, the present invention provides cell-containing enclosures configured for promoting tumor regression that are produced by the methods of the present invention. In other embodiments, the therapeutic protein promotes wound healing, and the enclosure produced is configured for promoting wound healing.

In particular embodiments, the present invention provides methods for producing a cell-containing enclosure for promoting tumor regression, comprising; a) providing, i) viable cells comprising a nucleic acid sequence encoding a therapeutic protein, wherein the therapeutic protein promotes tumor regression, and ii) an enclosure housing solid support material, wherein the enclosure comprises mesh material, and b) introducing the viable cells into the enclosure under conditions such that the viable cells attach to the solid support material. In preferred embodiments, the present invention provides cell-containing enclosures configured for promoting tumor regression that are produced by the methods of the present invention.

In some embodiments, the present invention provides methods for producing a cell containing enclosure for promoting tumor regression, comprising; a) providing, i) solid support material, ii) viable cells comprising a nucleic acid sequence encoding a therapeutic protein, wherein the therapeutic protein promotes tumor regression, and iii) an enclosure configured for housing the solid support material, wherein the enclosure comprises mesh material, and b) placing the solid support material into the enclosure, and sealing the enclosure, and c) introducing the viable cells into the enclosure under conditions such that the viable cells attach to the solid support material. In certain embodiments, the viable cells are injected into the enclosure. In other embodiments, the methods further comprise the step of freezing the enclosure containing the viable cells. In further embodiments, the methods further comprise the step of thawing the enclosure containing the viable cells. In other embodiments, the methods further comprise the step of thawing the enclosure containing the viable cells and maintaining the thawed enclosure in a tissue culture medium. In particular embodiments, the methods further comprise the step of performing a cell viability assay.

In certain embodiments of the present invention, the solid support material is treated with an composition giving the solid support material a negative charge (e.g. a net negative charge, or making the solid support material more negatively charged than the enclosure and/or tumor). In preferred embodiments, the solid support material is treated with a hydroxide solution (or similar solution) prior to placement (introduction) into the enclosure.

In some embodiments, the present invention provides enclosures configured for promoting tumor regression comprising mesh material having pores, wherein the enclosure houses viable cells on a solid support, wherein the viable cells comprise an expression vector, and wherein the expression vector comprises a nucleic acid sequence encoding a therapeutic protein useful for promoting tumor regression (e.g. IL-1, tumor necrosis factor alpha, etc). In certain embodiments, the vector encodes at least two therapeutic proteins (e.g. one cytokine and one tumor suppressor, or two cytokines, etc.).

In particular embodiments, the present invention provides systems and kits for promoting tumor regression, comprising; a) an enclosure configured for housing solid support material, b) solid support material, and c) a nucleic acid sequence encoding a therapeutic protein, wherein the therapeutic protein promotes tumor regression. In further embodiments, the system and kits of the present invention further comprise an insert component comprising writing instructions (e.g. how to assemble the components to produce a cell-containing enclosure capable of promoting tumor regression, and/or how to employ the system or kit to treat tumors). In other embodiments, the present invention provides systems and kits for promoting tumor regression, comprising; a) an enclosure configured for promoting tumor regression comprising mesh material having pores, wherein the enclosure houses viable cells on a solid support, wherein the viable cells comprise an expression vector, the expression vector comprises a nucleic acid sequence encoding a therapeutic protein, and b) an insert component comprising written instructions on how to use the enclosure to promote tumor regression in a subject. In certain embodiments, the various kit and system components are in separate containers or packages (e.g. separate vials). In some embodiments, the kits and systems of the present invention comprise a dressing (e.g. TEGADERM) that may be placed over the enclosure.

In certain embodiments, the therapeutic protein is a recombinant protein (e.g. the viable cells are transfected with a vector encoding the protein). In other embodiments, the therapeutic protein is naturally expressed by the viable cells (e.g. a cell line found or made to over-express a protein useful in promoting tumor regression).

In particular embodiments, the therapeutic protein is a cytokine, antibody, hormone, or steroid. In some embodiments, the therapeutic protein is a human or humanized antibody (e.g. Trastuzumab (HERCEPTIN) Genentech BioOncology/Roche, or Daclizumab (ZENAPAX), Protein Design Labs/Roche). In some embodiments, the therapeutic protein is a cytokine. In certain embodiments, the therapeutic protein is selected from interleukin-1, interleukin-2, interleukin-4, interleukin-6, interleukin-7, interleukin-10, interleukin-12, interferon-alpha, interferon-beta, interferon-delta, tumor necrosis factor-alpha, tumor necrosis factor-beta, granulocyte-macrophage colony stimulating factor (GM-CSF) and granulocyte colony stimulating factor (G-CSF). In particular embodiments, the therapeutic protein is a tumor suppressor protein. In certain embodiments, the tumor suppressor protein is selected from APC, BRCA1, BRCA2, CDH1, CKKN1C, CDKN2A, CYLD, EP300, EXT1, EXT2, MADH4, MAP2K4, MEN1, MLH1, MSH2, NF1, NF2, PRKAR1A, PTCH, PTEN, RB1, SDHD, SMARCB1, STK11, TP53, TSC1, TSC2, VHL, WT1, or combinations thereof. In preferred embodiments, the therapeutic protein comprises interleukin-1.

In certain embodiments, the viable cells comprise a nucleic acid sequence encoding the therapeutic protein. In particular embodiments, the nucleic acid sequence is exogenous. In some embodiments, the nucleic acid sequence encodes is a cytokine, antibody, hormone, or steroid. In some embodiments, the nucleic acid sequence encodes a humanized antibody (e.g. Trastuzumab, or Daclizumab). In certain embodiments, the nucleic acid sequence encodes a cytokine. In other embodiments, the nucleic acid sequence encodes a protein selected from interleukin-1, interleukin-2, interleukin-4, interleukin-6, interleukin-7, interleukin-10, interleukin-12, interferon-alpha, interferon-beta, interferon-delta, tumor necrosis factor-alpha, tumor necrosis factor-beta, granulocyte-macrophage colony stimulating factor (GM-CSF) and granulocyte colony stimulating factor (G-CSF). In particular embodiments, the nucleic acid sequence is a tumor suppressor gene. In certain embodiments, the tumor suppressor gene is selected from APC, BRCA1, BRCA2, CDH1, CKKN1C, CDKN2A, CYLD, EP300, EXT1, EXT2, MADH4, MAP2K4, MEN1, MLH1, MSH2, NF1, NF2, PRKAR1A, PTCH, PTEN, RB1, SDHD, SMARCB1, STK11, TP53, TSC1, TSC2, VHL, WT1, or combinations thereof. In some embodiments, the nucleic acid sequence is derived from the subject with the tumor (e.g., an IgG encoding nucleic acid sequence from the subject to be treated). In preferred embodiments, the nucleic acid sequence comprises a least a portion of the human interleukin-1 gene. In certain embodiments, the solid support material comprises beads. In preferred embodiments, the solid support comprises macroporous beads. In other embodiments, the beads comprise polyethylene. In certain embodiments, the beads further comprise silica. In other embodiments, the solid support material comprises a collagen coating. In particularly preferred embodiments, the solid support material comprises CYTOLINE 1 beads, or similar beads. In certain embodiments, the enclosure functions as the solid support material.

In certain embodiments, the viable cells are selected from fibroblasts, keratinocytes, endothelial cells, melanocytes, smooth muscles cells, fetal fibroblasts, macrophages, epithelial cells, stem cells (e.g., adult stem cells, embryonic stem cells), and combinations thereof. In some embodiments, the viable cells are derived from the subject. In other embodiments, the cells are mouse cells, human cells (e.g. human foreskin cells or derived from human foreskin cells).

In some embodiments, the mesh material comprises pores. In particular embodiments, the pores are large enough to permit viable cells on the solid support to cross the mesh material. In other embodiments, positioning the enclosure on the tumor allows less than 5%, 3%, or 1% of the viable cells to cross the mesh material. In certain embodiments, there are no detectable cells (e.g. by visual inspection) that pass from the enclosure onto the tumor. In some embodiments, the solid support material has a net negative charge. In other embodiments, the solid support material is more negatively charged than the mesh material. In preferred embodiments, the cells have a higher avidity for the solid support material than for the mesh material or the tumor.

In particular embodiments, the mesh material has pores ranging in size from about 1 micron to about 500 microns. In other embodiments, the mesh material has pores ranging in size from about 10 microns to about 400 microns. In preferred embodiments, the mesh material has pores ranging in size from about 10 microns to about 300 microns. In certain embodiments, the mesh material has pores with a size of approximately 300 microns (e.g. 295–305 microns). In certain embodiments, the pores are too small to permit the viable cells on the solid support to cross the mesh material. In some embodiments, the mesh material comprises polyethylene (e.g. a DELNET bag/material). In other embodiments, the mesh material is selected from polyester, nylon, or polyethylene.

In some embodiments of the methods of the present invention, the method further comprises a step of removing the enclosure from the tumor after regression of the tumor is promoted (e.g., after the size of the tumor has decreased, or there are no longer visible signs of a tumor). In particular embodiments, the enclosures of the present invention further comprise a removal component (e.g. string, handle, tab, or the like). In some embodiments, the methods of the present invention further comprise covering the enclosure (on the tumor) with a dressing. In particular embodiments, the enclosures of the present invention are sealable. In other embodiments, the enclosures are sealed.

In certain embodiments, the subject (e.g., with a tumor) is a mammal (e.g., human, cat, dog, cow, pig, etc.). In preferred embodiments, the subject is a human. In particularly preferred embodiments, the subject is a human with skin cancer. In some embodiments, the tumor (i.e. the tumor contacted with the cell-containing enclosure) is a cancerous tumor. In preferred embodiments, the cancerous tumor is skin cancer tumor (e.g. head and/or neck melanoma). In other embodiments, the tumor is a papilloma. In further embodiments, the tumor is wart.

A wide variety of tumors (e.g., cancer, papillomas and warts) can be treated by the methods, compositions, kits and systems of the present invention. Representative examples include, but are not limited to, colon carcinoma, prostate cancer, breast cancer, lung cancer, skin cancer, liver cancer, bone cancer, ovary cancer, pancreas cancer, brain cancer, head and neck cancer, lymphoma and other tumors. Representative examples of papillomas include, but are not limited to, squamous cell papilloma, choroid plexus papilloma and laryngeal papilloma. Representative examples of wart conditions include, but are not limited to, genital warts, plantar warts, epidermodysplasia verruciformis and malignant warts.

In certain embodiments, the present invention provides methods of generating enclosures with customer-specific characteristics. For example, the viable cells of the present invention may be transfected with a particular nucleic acid sequence specified by a user. As user, for example, may send an enclosure manufacturer information regarding the nucleic acid sequence to be used to transfect the cells (e.g. may communicate the name of a gene, or may send a sequence to be made), or a user may physically send the nucleic acid sequence to be used (e.g. as a source of the nucleic acid sequence to be used). In certain embodiments, information regarding the nucleic acid sequence to be used to transfect the viable cells is sent over the Internet (e.g. the sequence to be used is sent over the Internet or World Wide Web). In preferred embodiments, this information directs automated methods to produce enclosures containing solid supports with cells containing the user desired nucleic acid sequence. These enclosures, in some embodiments, are then shipped to the user (e.g. the enclosures are frozen or otherwise prepared for shipping and sent to a user, such as a doctor treating a patient with a tumor).

In other embodiments, the present invention is directed to systems and methods for enhancing the healing of wounds, including post surgical wounds and chronic wounds (e. g., diabetic wounds, pressure sores), involving the use of cultured cells. In some embodiments, the invention contemplates the use of cultured keratinocytes grown on a transplantable solid support. In other embodiments, the invention contemplates the use of transformed cells capable of secreting proteins beneficial in wound healing (e. g. cytokines and growth factors grown on a transplantable solid support).

The present invention is not limited by the nature of the transplantable solid support (solid support material); indeed, the present invention contemplates the use of any three-dimensional support or matrix to which cells will adhere, divide, and maintain their functional behaviors (e.g., heal wounds, or promote tumor regression). In some embodiments, the solid support comprises beads, and in further embodiments, the beads are macroporous. In the preferred embodiments, the solid support comprises polyethylene silica-coated beads. In particular embodiments, the beads are placed in an enclosure, compartment, bag, or similar barrier, the enclosure having pores, and the enclosure is then placed at the wound site for use as an interactive wound healing promoter.

The present invention is not limited by the nature of the enclosure; however, in one embodiment, the pores are large enough to permit the cells from the beads to exit the enclosure into the wound, while in another embodiment, the pores are too small to permit cells from the beads to exit the enclosure, but large enough to permit cellular factors to exit the enclosure or wound fluid components to enter the enclosure. In certain embodiments, the enclosures are replaced every few days until the wound heals (e.g., once a week).

In additional embodiments, the enclosure comprises a mesh material, having pores. In certain embodiments, the mesh material comprises polyethylene. In one embodiment, the pores are large enough to permit the cells from the beads to exit the enclosure into the wound, while in another embodiment, the pores are too small to permit cells from the beads to exit the enclosure, but large enough to permit cellular factors (e.g., cytokines) to exit the enclosure or wound fluid components to enter the enclosure.

Moreover, in further embodiments, the enclosure comprises a biocompatible membrane. In additional embodiments, the enclosure comprises means for removing the enclosure from a wound. In particular embodiments, the removal means comprises a handle or string attached to the enclosure.

In another embodiment, the present invention provides a system for the treatment of wounds, comprising a) keratinocytes on a solid support; and b) an enclosure, the enclosure housing the solid support. While the present invention is not limited to the nature of the keratinocytes, in a preferred embodiment the keratinocytes are viable and growing.

In another embodiment, the present invention provides systems and methods for enhancing the healing of wounds involving the use of transformed cells. The transformed cells may be any secretory cell, transformed with a gene encoding a protein beneficial in wound healing (e.g. a cytokine or growth factor). More specifically, a system for the treatment of wounds is provided comprising a) transformed cells on a solid support; and b) an enclosure, the enclosure housing the solid support.

The present invention also contemplates a method for treating a wound, comprising a) providing: i) keratinocytes on a solid support, ii) an enclosure, and iii) a subject having a least one wound; b) placing the keratinocyte-containing solid support into the enclosure so as to produce a keratinocyte-containing enclosure; and c) positioning the keratinocyte-containing enclosure in the wound of the subject under conditions such that the healing of the wound is promoted. Additional embodiments further comprise, after step b) and prior to step c), sealing the enclosure to produce a sealed keratinocyte-containing enclosure. Finally, some embodiments further comprise step d), covering the wound containing the keratinocyte-containing enclosure with a dressing.

The present invention further provides a method for treating a wound comprising a) providing: i) transformed cells on a solid support, ii) an enclosure, and iii) a subject having at least one wound; b) placing the transformed cell-containing solid support into the enclosure so as to produce a transformed cell-containing enclosure; and c) positioning the transformed cell-containing enclosure in the wound of the subject under conditions such that the healing of the wound is promoted. Additional embodiments further comprise, after step b) and prior to step c), sealing the enclosure to produce a sealed transformed cell-containing enclosure. Finally, some embodiments further comprise step d), covering the wound containing the transformed cell-containing enclosure with a dressing.

In some embodiments, the systems, methods, kits, and compositions are used to treat skin conditions (e.g., of a human). In certain embodiments, the skin condition is selected from psoriasis, vitiligo, atopic dermatitis, or hyperproliferative or UV-induced dermatoses.

In further embodiments, the present invention provides a process for manufacturing a bioactive means for treating a wound-site, tumor, or other tissue in need of treatment comprising the steps of providing a plurality of substantially solid cell-support means; a biocompatible enclosure means; a vehicle compatible with cell viability; and cells. In different embodiments of the invention, the steps vary in sequence.

In other embodiments, the present invention provides means for determining, at various stages of manufacture, (i) the viability of the cells, (ii) the distribution of viable cells on each one of the plurality of solid-support means; (iii) the distribution of viable cells as between the solid-support means and either the enclosure means or the vehicle; and (iv) the density of the cells on the solid cell-support means.

In some embodiments, the present invention provides methods for preparing an article comprising viable cells on an insoluble support comprising: a) providing an enclosure that is permeable to solutes; b) introducing into the enclosure an insoluble support material and sealing the enclosure; and c) introducing viable cells into the enclosure whereby the cells attach to the insoluble support material. In certain embodiments, the cells are injected into the enclosure. In other embodiments, the enclosure comprises a mesh material and the injection is performed through the mesh. In additional embodiments, the enclosure comprises a septum and the injection is performed through the septum.

In particular embodiments, the methods of the present invention further comprise freezing the enclosure containing the viable cells. In other embodiments, the methods further comprise thawing the enclosure containing the viable cells and maintaining the thawed enclosure in a tissue culture medium. In additional embodiments, the methods further comprise testing the viability of the cells by staining the cells with a dye that fluoresces upon binding of calcium and with a dye that fluoresces upon intercalation into DNA, then measuring the ratio of fluorescence of the calcium staining dye to the fluorescence of the DNA intercalating dye. In further embodiments, the methods further comprise testing the viability of the cells by staining the cells with a dye that fluoresces upon being hydrolysed by esterases (e.g. MDR1) and with a dye that fluoresces upon intercalation into DNA, then measuring the ratio of fluorescence of the esterase substrate dye to the fluorescence of the DNA intercalating dye. In other embodiments, mitochohdrial function assays are employed.

In some embodiments, the present invention provides methods for preparing an article comprising viable cells on an insoluble support comprising: a) providing an enclosure that is permeable to solutes but is impermeable to cells; b) introducing into the enclosure an insoluble support material and then sealing the enclosure in a biocompatible manner; c) introducing viable cells into the sealed enclosure by injection. In certain embodiments, the method further comprises testing the viability of the cells by sampling the cells within the enclosure and staining the cells with a dye that fluoresces upon binding of calcium (or serving as an esterase substrate) and with a dye that fluoresces upon intercalation into DNA, then measuring the ratio of fluorescence of the calcium staining dye (or esterase substrate dye) to the fluorescence of the DNA intercalating dye.

In particular embodiments, the present invention provides methods for preparing an article comprising viable cells on an insoluble support comprising: a) providing an enclosure that is permeable to solutes and to cells; b) introducing into the enclosure an insoluble support material; c) immersing the enclosure containing the support material into a culture of viable cells, whereby the cells migrate into the enclosure and attach to the support material. In further embodiments, the method further comprises removing the enclosure from the culture and freezing the article. In preferred embodiments, the support material is treated with a hydroxide solution prior to introducing the support material into the enclosure.

Definitions

Figure 1:
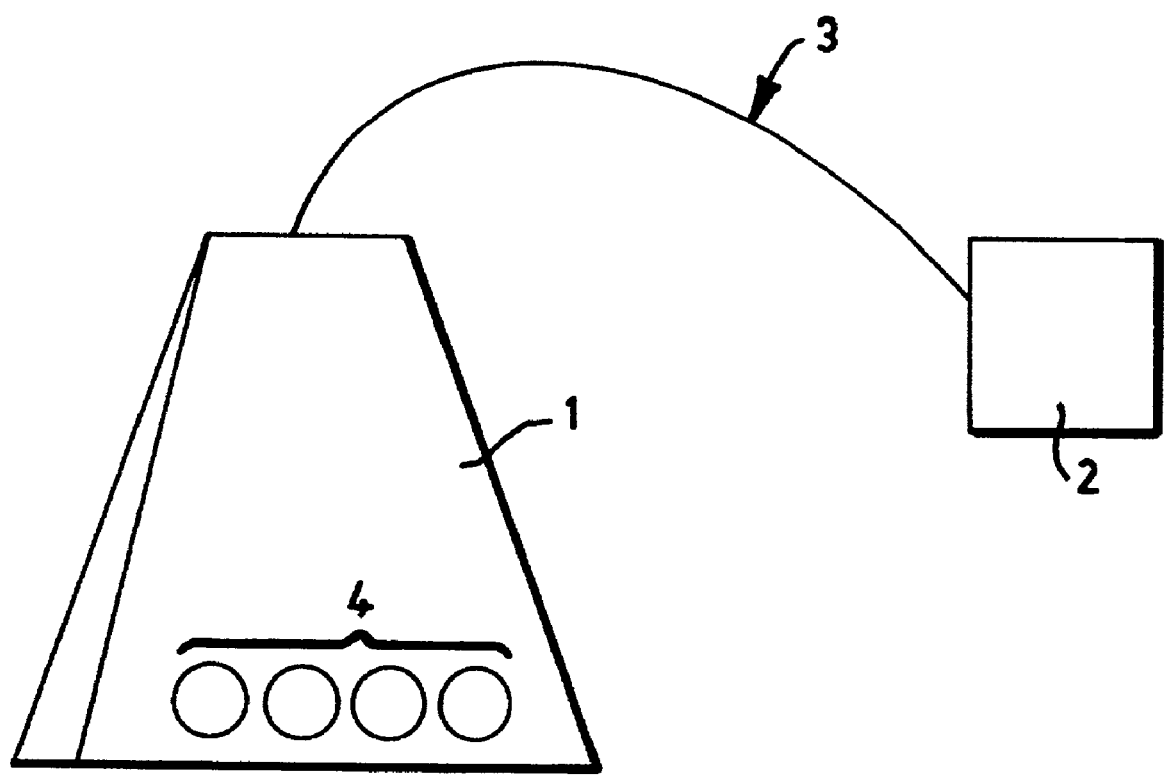
FIG. 1 diagrammatically depicts one embodiment of a tea bag contemplated for use with the cell-containing solid supports of the present invention.

To facilitate an understanding of the invention, a number of terms are defined below.

As used herein, the term "tumor" refers to an abnormal growth that arises from normal tissue, but that grows abnormally (e.g. abnormal growth rate and abnormal structure).

As used herein, the term "tumor regression" refers to any reduction in the size of a tumor. Examples of tumor regression include, but are not limited to, reducing the volume of a tumor by 5 percent, 10 percent, 20 percent, 40 percent, 50 percent, 75 percent, and 100 percent. By "promoting" regression, it is meant that some regression is detectable (e.g. greater than 5% reduction in tumor mass). It is not intended that the term "promote" suggest that the tumor completely regresses. It is sufficient that at least some regression is detectable.

The term "wound" refers broadly to injuries to tissue including the skin and subcutaneous tissue initiated in different ways, for example, surgery, (e.g., open post cancer resection wounds, including but not limited to, removal of melanoma and breast cancer etc.), contained post operation surgical wounds, pressure sores (e.g., from extended bed rest) and wounds induced by trauma. Wounds may also be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or fall-thickness wounds): wounds wherein bones are exposed (e.g., a bony pressure point such as the greater trochanter or the sacrum). The term "partial thickness wound" refers to wounds that encompass Grades I–III; examples of partial thickness wounds include bum wounds, pressure sores, venous stasis ulcers, and diabetic ulcers. The term "deep wound" is meant to include both Grade III and Grade IV wounds.

The term "chronic wound" refers to a wound that has not healed within 30 days.

The phrase "positioning the enclosure in the wound" is intended to mean contacting some part of the wound with the enclosure. The phrase "positioning the enclosure on the tumor" is intended to mean contacting some part of a tumor with the enclosure. "Contacting" includes, but is not limited to, bringing the enclosure proximate to the wound so as to bring the cells in fluidic communication with the wound.

The phrases "promote wound healing," "enhance wound healing," and the like refer to either the induction of the formation of granulation tissue of wound contraction and/or the induction of epithelialization (i.e., the generation of new cells in the epithelium).

The phrase "wound fluid contents" refers to liquid associated with a wound, as well as cells, cell factors, ions, macromolecules and protein material suspended in such liquid at the wound site.

The term "keratinocyte" refers to cells that produce keratin, a scleroprotein or albuminoid. Generally speaking, keratinocytes are found in the epidermis or from cell lines derived from keratinocytes (e.g., bacterial derived products).

The term "subject" refers to both humans and animals, including, but not limited to, a dog, cat, bird, livestock, and preferably a human. Specific examples of "subjects" include, but are not limited to, individuals with tumors, such as individuals diagnosed with skin cancer.

The terms "enclosure," "compartment," and the like refer broadly to any container capable of confining a cell-coated solid support within a defined location while allowing cellular factors to exit the enclosure into the wound or tumor, and wound or tumor fluid contents to enter. In preferred embodiments, the enclosure is a sterile mesh pouch constructed of a woven, medical-grade polyethylene mesh. In one embodiment, the present invention contemplates a degradable enclosure (i.e., an enclosure that breaks down over time). In addition, the present invention contemplates the use of an enclosure constructed from membranes. Preferably, after the solid support containing cells (e.g., growing on the surface of the surface of the solid support or within the solid support) is placed within the enclosure, the enclosure is sealed so as to prevent the solid support from exiting the enclosure. In one embodiment, the sealed enclosure further comprises a transport means for transporting cellular factors (e.g., outside of the enclosure and into the wound). While the present invention is not limited to a particular transport means, the transport means can include a means for applying pressure (e.g, a pump).

The terms "a solid support", "solid support", and "solid support material" are used interchangeably, and refer broadly to any support that allows for cell growth, including, but not limited to, microcarrier beads, gels, and culture plate inserts. Microcarrier beads suitable for use with the present invention are commercially-available from a number of sources, including, for example, Sigma, Pharmacia, and ICN. In preferred embodiments, the keratinocytes are grown on polyethylene beads weighted by silica (e.g., CYTOLINE 1 macroporous microcarrier beads (Pharmacia Biotech).

Culture plate inserts (i.e., cell support matrices that generally comprise a membrane that supports cell growth) are commercially available from, among other sources, Collaborative Biomedical Products, Costar, ICN, and Millipore. In preferred embodiments, the culture plate inserts comprise a permeable microporous membrane that allows free diffusion of ions and macromolecules.

The term "transplantable solid support" refers to a solid support containing cells (e.g., keratinocytes, referred to as a "keratinocyte-containing solid support") that can be placed within an enclosure. The enclosure containing the cell-containing solid support may then be placed in a wound to promote wound healing.

The phrases "means for removing," "removal means", "removal component" and the like refer broadly to any mechanism useful for assisting in the withdrawal of a cell-containing enclosure from a wound (and/or the placement of the cell-containing enclosure within a wound or on a tumor). In some embodiments, the removal means or component comprises a string, thread, cord, or the like that is attached to the enclosure; in preferred embodiments, the removal means or component is attached to a grasp that can be used as a handle to assist in the placement of the solid support containing enclosure within the wound (or on a tumor) and its removal therefrom.

The term "dressing" refers broadly to any material applied to a wound for protection, absorbance, drainage, etc. Numerous types of dressings are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer) [Kannon and Garrett, Dermatol. Surg., 21: 583–590 (1995); Davies, Burns, 10: 94 (1983)]. The present invention also contemplates the use of dressings impregnated with pharmacological compounds (e.g., antibiotics, anti-tumor compounds).

The term "biocompatible" means that there is minimal (i.e., no significant difference is seen compared to a control), if any, effect on the surroundings. For example, in some embodiments of the present invention, the enclosure comprises a biocompatible membrane; the membrane itself has a minimal effect on the cells of the solid support (i.e., it is non-toxic and compatible with keratinocyte growth) within the membrane and on the subject (i.e., it has no adverse impact on the subject's health or the rate of wound healing) after the enclosure is placed into a wound or on a tumor.

The term "extracellular matrix" refers broadly to material for supporting cell growth. It is not intended that the present invention be limited by the particular material; the present invention contemplates a wide variety of materials, including, but not limited to, material that is distributed throughout the body of multicellular organisms such as glycoproteins, proteoglycans and complex carbohydrates. The present invention contemplates the use of a substratum of extracellular matrix with the culture inserts on which the cells (e.g., keratinocytes) are plated. Although the present invention is not limited by the nature of the extracellular matrix, the preferred extracellular matrices include Matrigel, Growth Factor Reduced Matrigel, fibrillar collagen, lamininn, fibronectin and collagen type IV.

The terms "transformed cell" or "transfected cell" refer to a cell that has been transfected with a gene so that the protein encoded by the gene is expressed within the cell. In certain embodiments, the transfected cell is stably transfected. In a preferred embodiment, the cell is a secretory cell and the protein encoded by the gene is excreted from the cell. Examples of secretory cells include, without limitation, fibroblasts, keratinocytes, endothelial cells, melanocytes, smooth muscle cells, fetal fibroblasts and epithelial cells. It will be appreciated that more than one cell type, i.e., combinations of cells, may be employed. Cell lines (as opposed to primary cultured cells) may also be employed. It will be appreciated that a cell may be transfected with more than one gene so that more than one protein is expressed and excreted. Methods for producing transformed cells, i.e. transfection methods, are known by those skilled in the art and include, without limitation, the use of calcium phosphate coprecipitation, liposomemediated transfection, plasmid and viral vector-mediated transfection and DNA protein complex-mediated transfection and biolistic (e.g., gene gun) transfection. Viral vector mediated transfection includes, without limitation, the use of retroviral, replication deficient retroviral, adenoviral and adeno-associated viral vectors. Thus, a gene encoding a protein of interest may be introduced into a cell where it is expressed and secreted from the cell. Examples of "proteins of interest" (and the genes encoding same) that may be employed herein include, without limitation, cytokines, growth factors, chemokines, chemotactic peptides, tissue inhibitors of metallonproteinases, hormones, angiogenesis inhibitors, and apoptosis inhibitors. More specifically, preferred proteins include, without limitation, EGF, VEGF, FGF, PDGF, IGF, KGF, IFN-α, IFN-δ, MSH, TGF-α, TGFβ, TNF-α, IL-1 and IL-6 [See also Table 1 and Myers et al. Am. J. Surgery, 170: 75–83 (1995), hereby incorporated by reference].

As referred to herein, the term "encoding" is intended to mean that the gene or nucleic acid may be transcribed in a cell, e.g., when the nucleic acid is linked to appropriate control sequences such as a promoter in a suitable vector (e.g., an expression vector) and the vector is introduced into a cell. Such control sequences are well known to those skilled in the art.

As defined herein "operatively-linked" means that the nucleic acid (i.e., gene encoding a protein of interest) and an expression control sequence are situated within a vector or cell in such a way that the protein of interest is expressed by a cell which has been transformed (transfected) with the ligated nucleic acid/expression control sequence. Expression control sequences are known to those skilled in the art [See, e.g., Goeddel, Gene Therapy Expression Technology: Methods in Enzymology 185, Academic Press, San Diego, Calif. (1990)].

As used herein, the term "gene" means a nucleic acid which encodes a protein or functional fragment thereof. The term "nucleic acid" is intended to mean natural and synthetic linear and sequential arrays of nucleotides and nucleosides, e.g., in cDNA, genomic DNA (gDNA), mRNA, and RNA, oligonucleotides, oligonucleosides and derivatives thereof. It will also be appreciated that such nucleic acids can be incorporated into other nucleic acid chains referred to as "vectors" by recombinant-DNA techniques such as cleavage and ligation procedures. The terms "fragment" and "segment" as used herein with reference to nucleic acids (e.g., cDNA, genomic DNA, i.e., gDNA), are used interchangeably to mean a portion of the subject nucleic acid such as constructed artificially (e.g. through chemical synthesis) or by cleaving a natural product into a multiplicity of pieces (e.g. with a nuclease or endonuclease to obtain restriction fragments). The term "polypeptide" is used to mean three or more amino acids linked in a serial array.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

DESCRIPTION OF THE INVENTION

The present invention relates to devices, systems and methods for treating tumors. In particular, the present invention relates to enclosures housing cell-coated supports for promoting regression of tumors, such as cancerous tumors, papillomas, and warts. The present invention also relates generally to tissue healing and regeneration and, more particularly, to methods and systems for wound healing.

In preferred embodiments, the present invention provides methods of promoting tumor regression employing enclosures secreting therapeutic proteins. In certain embodiments, the enclosures house solid support material containing cells that are transfected with a gene encoding the therapeutic protein or proteins. One example of the tumor regression promoting abilities of the enclosures of the present invention is provided in Example 6. In this example, viable cells on solid support material are transfected with a gene encoding IL-1 and placed in an enclosure. The enclosure is placed on a tumor and promotes regression in the size of the tumor. Importantly, the enclosures of the present invention are capable of delivering therapeutic proteins for promoting tumor regression in an ex-vivo manner, thus avoiding the toxic affects many proteins have when delivered systemically. In certain embodiments, the therapeutic protein directly promotes tumor regression. In other embodiments, the therapeutic protein stimulates cells surrounding the tumor causing these surrounding cells to reduce the size of the tumor. In further embodiments, the therapeutic protein also stimulates an inflammatory response to help remove bacteria or other infectious organisms.

In other embodiments, the present invention involves the unique use of cultured cells to treat wounds, including post surgical wounds (e.g., open post cancer resection wounds and contained post operation surgical wounds) and chronic wounds (e.g, diabetic wounds). In preferred embodiments, cultured cells grown on transplantable solid supports are placed in a permeable enclosure; the enclosure is then placed in a wound. The cultured cells may be any cell type, including keratinocytes and/or transformed cells. Though a precise understanding of how the cell containing enclosure effects wound healing is not required in order to practice the present invention, it is believed that the cells in the enclosure secrete certain factors that enhance wound healing. The usefulness of the present invention has been demonstrated in athymic nude mice, an animal model routinely utilized in wound closure testing [See, e.g, Boyce et al., *Surgery,* 110: 866–76 (1991); Barbul et al., *Surgery,* 105: 764-69 (1989); and Hansbrough et al, *J. Burn Care Rehabil.,* 14: 485–94 (1993)].

It will be appreciated that the transformed cells of the present invention are not limited by the nature of the cells utilized nor by the genes employed to transform the cells. Examples of cells include, but are not limited to, the cells set forth in Table 1.

TABLE 1

| CELL TYPE | TISSUE | Cytokine, Growth Factor, Made/Responds To | Matrix Interactions | Wound Healing Potential |
|---|---|---|---|---|
| Fibroblast | Dermis Viseral Organs | TGF-beta, PDGF, IGF, IL-1, FGF, CTGF | Collagen type I, III, and IV, Elastin, Fibronectin, nidogen, SPARC, Osteonectin, Protenglycons, glucosamino-glycons, collagenases, gelatinase, stromelysin, TIMP, Thrombospondin | Fibroblast +4 |
| Endothelial Cell | Blood Vessels | FGF,VEGF, Endothelin, IGF, IL-1 | TIMP, GAG, Elastin, Laminin, Collagenase, Type IV Collagens, Fibronectin | Endothelial Cell +4 |
| Melanocyte Smooth Muscle Cell | Dermis Blood Vessels | IL-1, MSH PDGG, IGF, EGF, FGR | No ECM Production TIMP, GAG, Elastin, Laminin, Collagenase, Collagens, Fibronectin | Melanocyte +1 Fetal Fibroblast +4 |
| Epithelial Cell | Dermis Mucosa | FGF, TGF-alpha, TGF-beta, PDGF, IGF, IL-1, EFG, FGF, KGF IFN-gammama, TNF- | TIMP, GAG, Elastin, Laminin, Collagenase, Collagen type IV, VI, VII, laminins, Fibronectin, epiligrin, nidogen, elastin, | Epithelial Cell +4 |

TABLE 1-continued

| | |
|---|---|
| alpha, IL-1 alpha, activin | tenascin, thrombospondin, GAGs, proteoglycons, EMMPRIN, SPARC, uPA, PAI, collagenase, gelatinase, stromelysin |

ABBREVIATION GLOSSARY

| Cytokine, Growth Factors Made/Respond To | | Matrix Interactions | |
|---|---|---|---|
| TGF | Transforming Growth Factor | TIMP | Tissue Inhibitor of Metalloproteinases |
| PDGF | Platelet Derived Growth Factor | | |
| IGF | Insulin-like Growth Factor | GAG | Glucose Aminoglycons |
| IL | Interleukin | SPARC | Secreted Protein Acidic and Rich in Cysteine |
| FGF | Fibroblast Growth Factor | | |
| CTGF | Connective Tissue Growth Factor | ECM | Extracellular Matrix |
| VEGF | Vascular Endothelial Growth Factor | EMMPRIN | Extracellular Matrix Metalloproteinase Inducer |
| MSH | Melanocyte Stimulating Hormone | | |
| EGF | Epidermal Growth Factor | uPA | Urokinase Type Plasminogen Activator |
| KGF | Keratinocyte Growth Factor | | |
| IFN | Interferon | PAI | Plasminogen Activator Inhibitor |

I. Sources of Cells

The present invention is not limited by the source of the cells used, such as keratinocytes. In some preferred embodiments, the cells are obtained from living donors undergoing breast operations. In certain embodiments, prior to their use, the cells obtained from the donors are archived for at least six months, after which they are tested for the presence of viruses (e.g., hepatitis virus and HIV). In other preferred embodiments, the cells are cadaveric in origin. After the cells have been harvested from the cadaver, they are screened for viruses and other microbes prior to use.

Generally speaking, the keratinocytes contemplated for use with the present invention are primary cultured cells (i.e., the cells are not derived from cell lines) or are cells that have been transfected and developed into a keratinocyte derived cell line.

Example 1 in the Experimental section illustrates one embodiment of how keratinocytes may be isolated and processed for use with the present invention. However, it should be noted that the present invention is not limited to primary cultured cells.

Moreover, the present invention contemplates the use of cells that have similar characteristics to keratinocytes (e.g., cells that secrete growth factors, cytokines or keratin, whose behavior the cells utilize to promote wound healing). As described in detail herein, these cells may be derived from cells that are not keratinocytic in origin but have been modified by recombinant techniques, i.e. transformed cells.

II. Growth of Cells on Solid Supports

The cells contemplated for use with the present invention (e.g., keratinocytes and transformed cells) are grown on transplantable solid supports (solid support material). The present invention contemplates the growth of cells on solid supports, including protein-coated solid surfaces, as has been described in the art. For example, Gilchrest et al. [*Cell Bio Int. Rep.* 4: 1009 (1980)] describe the growth of keratinocytes on fibronectin-coated plates in the absence of a 3T3 monolayer, while Schafer et al. [*Exp. Cell. Res.* 183: 112 (1989)] describe a study of keratinocytes on floating collagen gels. Furthermore, Cook and Buskirk [In Vitro *Cell Dev. Biol.* 31: 132 (1995)] describe the growth of keratinocytes on a variety of matrices, including microporous membranes coated with collagen.

The present invention is not limited by the nature of the solid support. Indeed, the methods of the present invention may be practiced in conjunction with any support material that allows for cell growth, including, but not limited to, microcarrier beads, gels, and culture plate inserts. When microcarrier beads are desired, suitable beads are commercially available from a number of sources; for example, Sigma sells both collagen-and gelatin coated beads, Pharmacia sells dextran-based beads, and ICN advertises collagen beads. In preferred embodiments, the keratinocytes are grown on polyethylene beads weighted by silica (e.g., CYTOLINE 1 macroporous microcarrier beads (Pharmacia Biotech)).

Furthermore, culture plate inserts (i.e., cell support matrices that generally comprise a membrane that supports cell growth) are commercially available from, among other sources, Collaborative Biomedical Products, Costar, ICN, and Millipore. Such inserts frequently comprise polyethylene terephthalate, polycarbonate, TEFLON (Gore), and mixed cellulose esters. In particular embodiments, the culture plate inserts comprise a permeable microporous membrane that allows free diffusion of ions and macromolecules.

As indicated above, the present invention contemplates the use of transplantable solid supports. More specifically, in some embodiments, the present invention contemplates the application of keratinocyte-coated and transformed cell-coated solid supports, housed in an enclosure, to wounds and tumors. The use of cell-coated transplantable solid supports for application to wounds has been described in the art. For example, Hansbrough et al., *J. Am. Med. Assoc.* 262: 2125 (1989), describe collagen-glycosaminoglycan membranes covered with keratinocytes for wound application. [See also, Cooper et al., *J. Surg. Res.,* 48: 528 (1990); Ronfard et al. *Burns,* 17: 181 (1991); Tinois et al., *Exp. Cell Res.,* 193: 310 (1991); and Nanchahal and Ward, *Brit. J. Plas. Surg.* 45: 354 (1992)].

Generally speaking, growth of keratinocytes and other "anchorage-dependent cells requires attachment to a surface and spreading out in order to grow. Coventionally, such cells have been cultured on the wall of non-agitated vessels (e.g. tissue culture flasks) and roller bottles (e.g. U.S. Pat. No. 5,512,474, hereby incorporated by reference). Though not limited by the manner in which the cells are grown on solid supports, the present invention contemplates the use of these conventional techniques for growing cells on solid supports (see Example 1).

Other techniques for culturing solid support-bound cells are contemplated for use with the present invention. In some embodiments, the present invention contemplates the use of bioreactors for cell growth (See, U.S. Pat. Nos. 5,459,069 to Palsson et al., 5,563,068 to Zhang et al., both of which are hereby incorporated by reference.). Some bioreactors utilize hollow fiber systems. Frequently, bundles of parallel fibers are enclosed in an outer compartment; cells are grown on the outside surface of the fibers, while nutrient and gas-enriched medium flows through the center of the hollow fibers, nourishing the cells [See, e.g, U.S. Pat. No. 5,512,474 to Clapper et al., herein incorporated by reference].

In addition, bioreactors utilizing microcarriers (e.g., DEAE-derivatived dextran beads) can be used in conjunction with the present invention. In some embodiments, cell adhesion proteins like collagen, fibronectin, and laminin are used to anchor the cells to the solid support. Microcarriers may also incorporate an ionic charge to assist in cell attachment to the microcarrier. Frequently, the microcarriers are porous beads that are sufficiently large to allow cells to migrate and grow in the interior of the bead [See U.S. Pat. No. 5,512,474 to Clapper et al., hereby incorporated by reference].

In a particularly preferred embodiment, cells, are supported on a rigid support matrix (a semipermeable membrane) which allows for cell adherence and growth. The cells form a dense, three-dimensional array with large surface area which enhances modification of the fluid phase bathing the cells; the cell-populated matrix is constantly exposed to wound fluid components which diffuse into the reactor. The fluid can be modified and/or the cells can secrete mediators into the fluid to optimize the wound environment.

III. Enclosures

The present invention contemplates the placement of cell-coated (e.g., keratinocyte-coated) solid supports (e.g., beads) and transformed cell-coated solid supports (e.g., beads) in an enclosure, which, in turn, is placed in a wound or on a tumor. In preferred embodiments, the enclosure is a sterile mesh pouch constructed of a woven, medical-grade polyethylene mesh. Though not limited to mesh materials manufactured by any particular company, Tetko, Inc. and Saati manufacture mesh materials suitable for use with the present invention. The enclosures of the present invention may be colored or otherwise marked so that they may be easily identified in a wound or on a tumor.

Of course, other suitable materials (e.g., nylon, or other polymers) may also be used and are within the scope of the present invention. Indeed, any material that exhibits biocompatiblity when placed within a wound, or on a tumor, may be used with present invention. In addition, the present invention contemplates the use of an enclosure constructed from membranes, including the membranes sold commercially by Gelman Sciences and Millipore.

In a preferred embodiment, the enclosures are assembled as pocket-like containers with four edges and two surfaces. These containers may be manufactured in many ways (see, e.g., "Constructing Enclosures" section below). For example, the enclosure may be created by welding (e.g., uniting to create a seal) two pieces of material (of approximately equal dimensions) together on three edges. The fourth edge is left open to allow filling of the enclosure with the cell coated beads. The fourth edge is then sealed.

In an alternative embodiment, the enclosure may be manufactured from one piece of material by first folding that piece of material back onto itself. The region where the material overlaps itself may then be welded, resulting in the formation of a cylindrical tube. Thereafter, a pocket can be formed by welding closed one of the open ends of the cylinder, leaving the other end open for filling with the cell-coated beads; this enclosure design has the advantage of requiring one less weld.

The present invention is not limited to enclosures assembled as four-edged pockets nor is the invention limited to the techniques of constructing the enclosures disclosed above. For example, trapezoidal or circular enclosures may also be used in conjunction with the present invention.

For the assembly of the enclosures, the present invention contemplates the use of a variety of sealing techniques, including ultrasonic welding or heat welding. The technique of ultrasonic welding is well-known in the medical device-manufacturing art [See, e.g, U.S. Pat. Nos. 4,576,715 and 5,269,917, hereby incorporated by reference]. The present invention is not limited to a particular welding/sealing technique; indeed, any suitable sealing technique may be used with the present invention, including but not limited to ultrasonic, radiofrequency, heat, and impulse sealing.

In those embodiments comprising a mesh enclosure, the present invention is not limited by the pore size of the mesh. However, it should be noted that extremely small pores may retard or preclude the movement of materials out of the enclosure. The preferred range of pore sizes is from about 10 microns to about 300 microns. In particularly preferred embodiments, the pore size is about 300 microns (e.g., 290–310 microns). Likewise, if a membrane is used, the membrane should be permeable to the extent that it allows the cell factors to cross the membrane into the wound or onto a tumor.

In preferred embodiments, the solid support-containing enclosures of the present invention are configured like tea-bags (See, FIG. 1). That is, one end of a handle (3) (e.g., a biocompatible nylon material or excess from a heat seal, wire, etc.) is attached to the enclosure (1) housing the solid support (4), while the other end of the string is attached to a grasp (2). The grasp (2) is used as a "handle" to assist in the placement of the solid support-containing enclosure within the wound, or on a tumor, and its removal therefrom. The present invention is not limited by the material used to construct the grasp; in preferred embodiments, the grasp component (2) comprises a medical grade polyethylene material. Generally speaking, the grasp (2) is taped to the subject's skin at a site external to the wound. The solid support (4) has cells (e.g., keratinocytes) attached; it is preferred that such cells are viable.

IV. Transfer of Cell Factors

Following placement of the enclosure within the wound, or on a tumor, the cell factors including proteins of interest (e.g, growth factors like epidermal growth factor, cytokines, PGDF, insulin like growth factor, TGF-beta, keratinocyte growth factor cytokine, TNF, chemokines, chemotactic peptides, tissue inhibitors of metalloproteinases, etc.) secreted from the cells (e.g., keratinocytes and transformed cells) pass through the enclosure and into the wound, or onto a tumor. The inventors of the present invention have found that it is not necessary for the cells to be in direct contact with the wound. Though an understanding of why such indirect contact is sufficient for wound healing is not required in order to practice the present invention, it is believed that the donor cells (i.e., those contained within the enclosure) create a favorable environment for growth of the keratinocytes present in the wound of the subject. Thus, the keratinocytes from the healed wound site are thought to be of recipient, rather than donor, origin [See Van der Merve et al., *Burns,* 16: 193 (1990)]. In addition, the cells may actively modify wound fluid characteristics or components (e.g., modulating proteolytic activity to optimize the wound environment).

The inventors of the present invention discovered empirically that placement of cell-coated solid supports within the enclosures (described above) resulted in good size reduction of deep wounds; in comparison, researchers previously reported less than ideal healing in deeper wounds [Van der Merve et al., *Burns* 16: 193 (1990)] when other techniques were used.

The inventors have found that the use of the present invention in conjunction with standard wound dressing materials does not adversely affect the ability to modify the wound environment. For example, after placing the keratinocyte-containing enclosures or transformed cell-containing enclosures within a wound, the enclosure can itself be covered with occlusive dressings such as hydrogels, foams, calcium alginates, hydrocolloids, and films. Example 2 of the Experimental section addresses an embodiment wherein a keratinocyte-containing enclosure is covered by a wound dressing.

V. Therapeutic Proteins and Genes

As mentioned above, the present invention contemplates transfecting cells with nucleic acid sequence (e.g. at least a portion of a human gene sequence), such that the cells express at least one therapeutic protein for promoting wound healing or treating tumors (e.g. promoting tumor regression). In some embodiments, the cells are transfected with at least one type of cytokine gene. Examples of cytokine genes (with corresponding GENBANK accession numbers) include, but are not limited to, interleukin-1 (alpha, NM_000575; beta, NM_000576), interleukin-2 (NM_000586), interleukin-4 (NM_000589), interleukin-6 (NM_000600), interleukin-7 (NM_000880), interleukin-10 (NM_000572), interleukin-12 (12A, NM_000882; 12B, NM_002187), interferon-alpha (NM_024013), interferon beta (NM_002176), interferon-delta, tumor necrosis factor alpha (NM000594) and beta (NM_009588), granulocyte-macrophage colony stimulating factor (GM-CSF), and granulocyte colony stimulating factor (G-CSF).

Nucleic acid sequence which inhibit expression of oncogenes such as HER-2/neu (e.g., the tumor suppressor E1A from adenovirus 5), or which control cell growth or differentiation are also preferred for transfecting cells of the present invention. For example, nucleic acids which encode expression of inflammatory molecules, cytokines, growth factors, telomerase, growth factor receptors, oncogene products, interleukins, interferons, alpha-FGF, IGF-I, IGF-II, beta-FGF, PDGF, TNF, TGF-alpha, TGF-beta, EGF, KGF, SCF/c-Kit ligand, CD40L/CD40, VLA-4/VCAM-1, ICAM-1/LFA-1, and hyalurin/CD44; signal transfection molecules and corresponding oncogene products, e.g., Mos, Ras, Raf, and Met; and transcriptional activators and suppressors, e.g., p53, p21, Tat, steroid hormone receptors such as those for estrogen, progesterone, testosterone, aldosterone, and corticosterone or the like are known, preferred, and widely available. Nucleic acids which encode inhibitors of such molecules are also preferred, such as ribozymes and antisense RNAs which recognize and inhibit translation of the mRNA for any of the above.

In further embodiments, the cells of the present invention are transfected with tumor suppressor genes. Examples of tumor suppressor genes include, but are not limited to, APC, BRCA1, BRCA2, CDH1, CKKN1C, CDKN2A, CYLD, EP300, EXT1, EXT2, MADH4, MAP2K4, MEN1, MLH1, MSH2, NF1, NF2, PRKAR1A, PTCH, PTEN, RB1, SDHD, SMARCB1, STK11, TP53, TSC1, TSC2, VHL, WT1, or combinations thereof.

VI. Tumor Susceptibility Assays

The present invention also provides tumor susceptibility assays. Preferably, the tumor susceptibility assays of the present invention are employed to help select one or more therapeutic proteins likely to promote tumor regression in particular tumors. In this regard, the cells of the present invention may be transfected with a nucleic acid sequence or sequences encoding a therapeutic protein likely to be useful in promoting tumor regression for specific tumors. The tumor susceptibility assays allow, for example, the enclosures of the present invention to be "customized" for a particular patient, thus improving the effectiveness of the tumor treating abilities of the enclosures of the present invention.

In certain embodiments, tumor susceptibility assays are performed by surgically removing a portion a subject's tumor, and growing a least a portion of the tumor in culture. The explanted tumor culture may then exposed to solid support material (e.g. beads) containing cells expressing one or more candidate therapeutic proteins (e.g. cells expressing one or more cytokines). Inhibition, or non-inhibition, of the tumor cells is then detected. In preferred embodiments, a least a portion of the subject's tumor is grown in tissue culture media. In other preferred embodiments, a primary culture is established with the tumor cells prior to further manipulation. In some preferred embodiments, the cells on the solid support material expressing the candidate therapeutic protein are mouse macrophage cells. In certain embodiments, the solid support (e.g. beads) populated with transfected cells are primed using culture media from the tumor of being assay. In other embodiments, the solid support material populated with transfected cells are co-cultured with the tumor cells.

In particular embodiments, the present invention provides methods comprising, a) providing; i) viable cells on a solid support, wherein the viable cells secrete at least one candidate therapeutic protein, ii) a tumor sample comprising cancer cells, wherein the tumor sample is derived from a subject's tumor, b) contacting the viable cells with the tumor sample under conditions such that the cancer cells' susceptibility to the candidate therapeutic protein is determined. In some embodiments, a control is also run where viable cells not secreting a therapeutic protein (e.g. not transfected with a nucleic acid sequence encoding the therapeutic protein) are assayed in the same manner as the viable cells that are secreting a candidate therapeutic protein. In preferred embodiments, once cells (on solid support material) are identified as likely to cause tumor regression/destruction, this type of cell is packaged into the enclosures of the present invention and employed on the subject's tumor or tumors (e.g. contacted with the subject's tumors for 2 hours, 4 hours, 12 hours, 24 hours, 2 days, a week, etc).

In particular embodiments, the subject's tumor is not removed surgically, and instead, a enclosure of the present invention containing solid support material with cells expressing a candidate therapeutic protein is contacted directly with the subject's tumor. In similar embodiments, the tumor cells are grown in an immuno-incompetent test animal (generating a tumor), and the enclosure is contacted with the tumor directly (See, Example 7). In certain embodiments, the ability of the enclosure (containing the cells secreting the candidate therapeutic protein) is determined by removing the enclosure from the tumor after a period of time (e.g. one day, two days, one week, etc.). The effectiveness of the enclosure in promoting tumor regression may be determined by examining either the tumor (e.g. to see if it has reduced in size), or examining (or further manipulating) the enclosure. For example, as shown in Example 7 below, the amount of tumor cells that have invaded the solid support material may be examined.

The ability of the enclosure to promote tumor regression may be established, for example, if tumor cells are unable to significantly invade the solid support material. Conversely, if tumor cells are able to invade the solid support material, even in the presence of the cells secreting the candidate therapeutic protein, it is unlikely that the enclosure will promote significant tumor regression. However, this will inform the user that a different candidate therapeutic protein should likely be assayed in an attempt to identify therapeutic proteins (and enclosures) for particular patients.

Tumor susceptibility to a particular treatment may also be determined by performing DNA or RNA diagnostic assays on a patient's normal cells or tumor cells. In this regard, variations in a particular subject's tumors or normal cells may be employed to selected nucleic acid sequences encoding proteins likely to be useful in promoting tumor regression. Specific methods for nucleic acid variation detection include DNA sequence determination (Sanger method with either radionuclide or fluorescence label, Maxam and Gilbert Method, HPLC, or other methods) through use of manual, semi-automated, or automated processes including use of gels or capillaries, Mass Spec-based technologies including MALDI-TOF MS, spectral assays, technologies aimed at detection of different melting temperatures for sequences that differ from each other, technologies based on use of confocal or de-convoluting microscopy to evaluate fluorescence labeled DNA, RNA, or DNA/RNA hybrids, via affinity sensor using surface plasmon resonance technologies, PCR and RT-PCR, use of other clone-based, polymerase-based, or PCR based technologies to detect hybridization in simplex or multiplex technologies, electronically active microfabricated array technologies such as APEX microchips, electrical field denaturation, microplate array diagonal gel electrophoresis (MADGE), amplification including TAQMAN technologies, measurements of sequence-base changes in electron transfer through the DNA helix, gene-chip assays involving high density oligonucleotide arrays including Affymetrix-like technologies, microarray technologies, ribotyping, pulsed-field gel electrophoresis (FAGE), field alternation gel electrophoresis (FAGE) and related technologies, allele-specific or differential PCR amplification, hybridization-based technologies including Southerns, Northerns, dot-blots and slot-blots, double- or triple-helix formation, dual-label fluorescence assays of differential hybridization of DNA, amplified fragment length polymorphism-based fingerprinting (AMF), confirmation variation based technologies such as single strand confirmation polymorphism (SSCP) or GC-clamped denaturing gradient gel electrophoresis or other variations on this concept that evaluate conformational differences in DNA, RNA, or DNA/RNA hybrid structures, other rapid scanning technologies based on screening for sequence mismatches through detection of DNA, RNA, or DNA/RNA hybrids containing mismatched or altered base-pairing including use of altered mobility through capillaries or acrylamide-based, agarose based, MDE or other forms of gel technology, additional rapid scanning technologies based on detection of DNA, RNA, or DNA/RNA hybrids with mismatched or altered base pairing via cleavage at, or other form of digestion of the target through either enzymatic or chemical methods, or polymerase-based extension from, mismatched or altered base pairing of DNA, RNA, or DNA/RNA hybrids, primer-extension-based technologies, allele specific oligonucleotide hybridization, or cutting of cloned or PCR-amplified segments of the gene with restriction enzymes. This use of sequences in screening includes not only use of coding sequences but also use of intronic sequences, flanking portions of unprocessed and processed transcripts, adjoining regions including promoters and other sequences 3' and 5' to the gene. For a review of detection methodologies, see Shi, Clinical Chemistry, 47:2, 164–172 [2001], discussing, for example, TAQMAN, Rolling Circle, and INVADER assays, this review hereby incorporated by reference, see also, U.S. Pat. Nos. 6,150,104 and 6,210,884 for suitable detection methods, both of which are hereby incorporated by reference.

Examples of subject's tumors that may be assayed include, but are not limited to, any solid tumor, melanoma, breast, pancreas, colon, stomach, bladder, ovary, bone, kidney sarcomas or carcinomas. The subject's tumor that is surgically removed may, for example, be either recurrent or primary.

Any method may be used to determine the affect (e.g. inhibition or non-inhibition) of the transfected cells on the tumor. In some embodiments, inhibition of the tumor is determined using a lines of growth inhibition assay, or an examination invasion of the solid support by tumor cells, or by death of the tumor culture.

In certain embodiments, the present invention provide kits comprising two or more components useful for performing tumor susceptibility assays. In certain embodiments, the kits comprise instructions for performing a tumor susceptibility assay, and one other component (e.g. enclosures, solid support material, cells configured for secreting one or more therapeutic proteins, etc.).

VII. Constructing Enclosures

The present invention also provides methods for constructing enclosures. U.S. Provisional Application No. 60/149,744, and U.S. patent application Ser. No. 09/640,990, both of which are hereby incorporated by reference for all purposes, describe methods of making enclosures useful in the present invention. Enclosures and methods of making enclosures are also provided, for example, in U.S. Pat. No. 5,972,332, as well as U.S. patent applications Ser. Nos. 09/323,188 and 09/502,479, all of which are hereby incorporated by reference for all purposes.

In constructing enclosures, any solid-support means capable of sustaining a living cell (e.g., within the meaning of the viability test disclosed herein) may be selected for use by the skilled practitioner of this invention. In preferred embodiments, solid supports will be selected to provide adequate surface area to accommodate cell attachment and growth to a sufficiency for the purposes of the invention. In preferred embodiments, solid supports will be selected to be of such a shape and size as to be substantially incapable of permeating the selected enclosure. It is not intended, however, that such impermeability be achieved solely by the shape or size of the solid supports. Other properties, such as the degree of hydrophilicity and hydrophobicity, the electrical charge properties, and the lipophilicity or polarity of either the solid supports or the enclosure means may also be employed to achieve the preferred impermeability.

In some embodiments, to promote cell-seeding and/or cell viability, solid-support material is treated or coated with biocompatible substances to render them more or less hydrophilic or hydrophobic, cationic or anionic, polar or non-polar are also contemplated to be within the scope of this invention.

Any biocompatible enclosure means (material) capable of substantially retaining the selected cell-support means (material) may be selected by the skilled practitioner of this invention. P530 Natural (AET, Inc.) is a specific example. In preferred embodiments an enclosure means that is generally permeable to solutes will be selected. In certain embodiments an enclosure means that is permeable to cells in at least one direction will be preferred. In certain embodiments enclosure means that resist attachment of cells to one or both of their surfaces are preferred. In certain embodiments, the enclosure means is sealable in such a way that a biocompatible seal results. In certain embodiments, the skilled practitioner will select an enclosure means and a sealing means such that the enclosure means and the seal remain useful for the purposes of the invention after being subjected to temperatures adequately high to sterilize the enclosure means or adequately low to preserve cell viability by means of freezing.

The properties enumerated in the foregoing are exemplary and, in general, do not need to be combined in any particular aggregation to effect a useful embodiment of the invention. Thus, cells may be introduced into a pre-sealed enclosure by means of injection or by effecting immigration of cells through a cell-permeable enclosure means. Alternatively, cell-support means and cells may be introduced into a sealably open enclosure. The cell support means, moreover, need not be seeded with cells when the cell support means is introduced into the enclosure. Indeed, embodiments are contemplated wherein at least a portion of the cell-support means and at least a portion of the cells in each manufactured article are introduced into, and reside in, the enclosure in separate compartments. Compartmentalization may be achieved by a physical barrier such as a membrane, or by segregating the support means and the cells in separate vehicles, which vehicles are rendered immiscible by virtue of having been frozen separately, or suspended in immiscible gels. The skilled practitioner may select from a number of cell culture media known to support cell growth. The selection, for which the skilled practitioner will have ample guidance from the prior art, will depend upon the cell-type and specific conditions chosen to prepare the cell culture.

Generally, the selection of cells depends upon the bioactive treatment intended. For example, keratinocytes derived from breast tissue, foreskin, abdominal full or split thickness skin, or the skin of cadavers are useful in the treatment of wounds. Other acceptable primary cell types include, without limitation, fibroblasts, melanocytes, endothelial cells, blood-borne cells, and osteocytes. Any cell transformed by the insertion of DNA by any means that results in a cell capable of secreting an expression product of the inserted DNA, or a product whose expression by the cell is promoted or enhanced by the insertion of the DNA is also suitable. The particular DNA to be selected will depend upon the treatment to be applied. An ample literature exists to provide guidance to the skilled practitioner in this regard. In preferred embodiments, the cells are transfected after being seeded on to the solid support material.

In some embodiments, a cell viability assay is performed on the cells. In certain embodiments, the cell viability assay is performed before the cells are seeded onto the solid support material. In other embodiments, a cell viability assay is performed after the cells are seeded on the solid support material. In preferred embodiments, a cell viability assay is performed after the cells on the solid support are placed in an enclosure. Any type of cell viability assay may be used with the present invention. In some embodiments, the cell viability assay comprises a mitocondrial function assay.

VIII. Enclosures with Monitoring Devices

In certain embodiments, the enclosures of the present invention contain, or are otherwise attached to, one or more monitoring devices. These devices may be used with the enclosures of the present invention to monitor the status of the condition being treated by the enclosure. For example, in addition to the enclosure contacting a wound or tumor, the monitoring device may also contact the wound or tumor. In this regard, the progress of treatment (e.g. promotion of wound healing, or tumor regression) may be monitored without the need for visual inspection and/or other medical tests. This allows both constant monitoring, and reduces the need for the subject (or the subject's physician) to remove the enclosure to inspect the wound, tumor, or other condition.

The monitoring device may be any device capable of collecting information about a subject's condition (e.g. size of wound or tumor, temperature of subject, ion concentrations, pH, etc), and displaying this information (e.g. on a LCD display, or by transmitting this information to a receiver). In preferred embodiments, the information collected by the monitoring device is transmitted over the Internet to the subject's physician or other health care professional. Examples of monitoring devices are provided in U.S. Pat. No. 4,763,659 to Dunsearth Jr., U.S. Pat. No. 6,070,103 to Ogden, and U.S. Pat. No. 5,836,989 to Shelton, all of which are herein incorporated by reference for all purposes. In certain embodiments, the cells (on the solid supports) in the enclosures are modified (e.g. with a reporter or recorded gene) in order to work with the monitoring device. In a preferred embodiment, the enclosures of the present invention can be attached to monitoring devices comprising electronic sensors and placed into a skin wound. In other preferred embodiments, the electronic sensors can determine temperature, viscosity, lactic acid, pH, Na+ K+, oxygen, specific gravity, or other wound products known to be toxic to the wound.

Experimental

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); DS (dextran sulfate); C (degrees Centigrade); and Sigma (Sigma Chemical Co., St. Louis, Mo.).

EXAMPLE 1

The experiments of this example demonstrate that human culture keratinocytes grown on macroporous microcarriers and contained in a porous enclosure improve healing in surgically created wounds in mice.

A. Experimental Methodology

Preparation of Human Keratinocytes

Isolation and Growing of Human keratinocytes: Human keratinocytes (AATB certified; University of Michigan cultured keratinocyte program) were isolated at The University of Michigan Burn/Trauma Unit from split thickness skin.

Trypsinization of the split thickness skin was effected as follows. The skin was placed dermis-side down in 150 mm Petri dishes. The pieces were cut into smaller pieces (about 2 cm×about 0.3 cm) and were soaked in a sterile solution of 30 mM HEPES, 10 mM glucose, 3 mM KCl, 130 mM NaCl, 1 mM $Na_2HPO_4$ buffer, pH 7.4 containing 50 units of Penicillin and 50 μg Streptomycin (Sigma, P-0906). After soaking for 1–2 hr at 4° C. the buffer was aspirated off, and 0.09% trypsin (Sigma, Type IX) in a Penicillin and Streptomycin buffer was added to the dishes containing the skin tissue.

After trypsinizing overnight at room temperature, the enzyme solution was aspirated off, and complete MCDB 153 (Gibco, Grand Island, N.Y.) medium containing trypsin inhibitor was added to the skin pieces. Complete MCDB 153 medium was made by supplementing basic MCDB 153 (Gibco, Grand Island, N.Y.) medium, prepared as described by Boyce and Ham ["Normal human epidermal keratinocytes," In In Vitro Models for Cancer Research (Weber and Sekely, eds.) CRC Press, Boca Raton, Fla., pp. 245–274 (1985)], with 0.6 μM (0.218 μg/mL) hydrocortisone, 5 ng/mL epidermal growth factor, 5 μg/mL insulin, 6% bovine pituitary extract, and 0.15 mM $CaCl_2$.

The dermis was separated from the epidermis, and the epidermal basal cells were gently scraped off both segments of the skin. The cell suspension was pooled into 50 mL conical centrifugation tubes, gently centrifuged at room temperature, and resuspended in 50 mL of complete medium plus 2% chelated serum.

The cells were counted using a hemacytometer, and $20\times10^6$ cells were plated into a T-75 Corning Plastic flasks and grown at 37 C with 5% $CO_2$ gassing, using a humidified incubator. After 3 days, the used growth medium was removed and complete MCDB 153 without serum was added. The cells were fed every other day.

The cells were passaged during log phase of growth. Thereafter, the cells were trypsinized using 0.025% trypsin (type IX) plus 0.01% EDTA in the HEPES buffer. The monolayers were washed with the buffer twice, then 2–3 mL of freshly-made enzyme solution (or frozen aliquot) were added. After 1 min. at 37 C, the enzyme solution was gently aspirated off, and the cells were placed in flasks at 37 C for 2–3 min. until the cell sheets came off the bottom with gentle tapping of the flask. The media was neutralized with 1–3 mL of MCDB 153 medium plus 0.03% trypsin inhibitor (Sigma). The cells were counted, centrifuged, and plated 0.5 to $1.0\times10^6$ cells per T-75 flask. Cells were passaged 3 to 4 times.

CYTOLINE 1™ Bead Wash: Five grams of CYTOLINE 1™ macroporous microcarrier beads (Pharmacia Biotech) were autoclaved for 10 min. in 40 mL Milli Q water (Millipore, Bedford, Mass.) in a 125 ml Erlenmeyer flask. Following the autoclaving procedures, the beads were cooled and the water was aspirated. The beads were resuspended in 40 mL Milli Q water, and were then agitated at moderate speed on a Labline orbital shaker for 10 min. The water was again aspirated, and a final washing with 40 mL Milli Q water was performed.

The beads were transferred into a 50 mL conical culture tube, the water was aspirated, and 30 mL 0.1 N NaOH were added. The beads were incubated at room temperature overnight. The NaOH solution was aspirated off the beads, and the beads were resuspended in 50 mL Milli Q water. The aliquot was transferred to a 125 Erlenmeyer flask and shaken at moderate speed for ten minutes. The Milli Q water was aspirated off the beads, and the beads were resuspended in Milli Q water; this aspiration/resuspension procedure was repeated a total of five times. The pH was neutral (i.e., less than 8), as measured with pH paper.

The beads were aspirated and resuspended in 40 mL PBS without $Mg^{2+}$ and $Ca^{2+}$, and autoclaved 30 min. at 121 C.

Growth of Keratinocytes on CYTOLINE 1™ Beads: A slurry containing 10 mL of PBS solution and 5 g of beads (contained in a 50 mL sterile conical centrifuge tube) was autoclaved as described above. The PBS was decanted, and 50 mL of MCDB 153 complete medium was added to the beads. The cells were conditioned in the medium at 37 C with 5% $CO_2$ gas for 48 hours.

The medium was decanted, and the beads were transferred into a separate 50 mL sterile centrifuge tube. Ten-to-15 mL of medium were added, and the suspension was centrifuged at 1000 rpm for 3 min. The medium was again decanted, and $30\times10^6$ breast cells (from a living donor passage 1, never frozen) were added. After gently agitating the cells with the beads for 5 minutes, the cells and beads were poured into a 250 mL glass roller bottle and 50 mL of medium was added; this was performed using a fermentor-agitated growth system.

As a toxicity assay, 5 mL of cells and beads were removed from the glass roller bottle and grown in a T-25 flask to determine the growth of the cells on the plastic bottom of the flask in the presence of the beads. The roller bottle was incubated overnight at 37 C, after which 100 mL additional medium was added to the roller bottle and the rotation of the roller bottle was initiated (rotation rate=one turn/15 sec.).

To feed the cells, an aliquot of medium was removed and replaced by fresh medium, adjusted to the correct pH with $CO_2$ gassing. The cells were fed every 48 hours.

Experimental Design

An eight-day animal trial was conducted with two groups of ten animals each. The wound dressings (see below) were changed every other day starting on day 0. Wound area measurements and photographs were obtained at days 0, 2, 4, 6, and 8.

All surgical procedures were performed under sterile conditions inside a laminar flow hood. Five-week old, female Nu/J mice (Jackson Labs) were used. Nu/J mice contain a recessive mutation found on chromosome 11 and are athymic (T-cell deficient). The mice have a reduced lymphocyte count comprised almost entirely of B-cells, a normal IgM response to thymus-independent antigens, a poor response to thymus antigens, increased macrophage and NK cell activity, and increased susceptibility to infection. Nu/J mice do not reject allogeneic and xenogeneic skin and tumor grafts.

The mice were anesthetized with metofane (Mallinckrodt Veterinary) and prepped with ethanol. Using fine surgical scissors, a fall thickness surgical wound approximately 80 $mm^2$ in area was created on the backs of the mice (the depth of the wound could be measure through the *panniculus carnosis*, but mouse skin is so thin so it was not used as an indicator here). The wound dressings (see below) were secured to the cephalad end of the wound with a surgical staple. Thereafter, each mouse was returned to its biohazard containment cage.

On days 2, 4, 6 and 8, the animals were returned to the laminar flow hood for removal of the staple and replacement of the bag. The animals were lightly restrained while area and photographic measurements were obtained (described below). The dressing was replaced and secured; all dressing changes were performed using sterile technique without general anesthesia.

Wound Dressing

The wounds were dressed either with human cultured keratinocytes grown on beads (keratinocytes/beads) in a DELNET bag (P530 Natural; AET, Inc.) or a DELNET bag alone (P530 Natural; AET, Inc.); the DELNET bags were approximately square (about 23 mm×25 mm). The seams of the bags were prepared with an Impulse heat sealing unit (American International Electric Co.). Prior to application on the mice, the DELNET bags were gas sterilized with ethylene oxide and placed in a sterile package. A BANDAID (3M Healthcare) covered the DELNET bags and was secured with surgical staples (Richard-Allen, Inc). The bag was stapled to the BANDAID, and the BANDAID was stapled to the mouse.

The bag and bead assembly was performed in a tissue culture hood. Inside a laminar flow hood, the keratinocytes/bead suspension was transferred to the DELNET bag with a glass pipet. Approximately 250 μL of the keratinocyte/bead suspension was placed in the bag. After the beads were loaded into the bag, the final seam was made with a surgical needle holder heated in a glass bead sterilizer. The DELNET bag containing the keratinocytes/bead suspension is referred to as "beads/bag," while the DELNET bag without the beads is referred to as "bag." The bags and beads/bags were placed in the complete MCDB 153 medium described above after they were loaded and heat sealed.

Measurement of Wound Area

Total area of mouse wounds was performed as previously described [Schwarz et al., Wound Repair and Regeneration 3:204–212 (1995)]. Briefly, the area of the wound was traced on transparency film (Apollo, Ronkonkoma, N.Y.) with a fine marker. The transparency film was photocopied onto plain paper and subsequently scanned into a PIC file with a Lightning Scan Pro 256 hand scanner (Thunderware). Tissue area was calculated with non-rectangular area analysis used by NIH image 1.58, and the data was expressed as millimeters squared. Mean and standard deviation were calculated using Statworks software (a statistically significant difference was $p<0.05$).

B. Experimental Results Table 2 presents wound tissue area ($mm^2$) at baseline (day 0) and at days 2, 4, 6, and 8 for each mouse which received bags containing keratinocyte-coated beads (beads/bags); the reduction in size of the wound as a percentage of the original wound size for each mouse is also set forth. Analogous data for the mice that received bags alone is presented in Table 3.

Table 4 presents the cumulative data for i) the beads/bags mice and ii) the bags only mice.

TABLE 2

| Day 0 size ($mm^2$) | | |
| --- | --- | --- |
| cells/bag | mean | 106.1 |
|  | SD | 35.3 |
| cells/bag tegaderm | mean | 103.1 |
|  | SD | 15.8 |
| tet cells/bag | mean | 90.7 |
|  | SD | 40.5 |
| tet cells/bag tegaderm | mean | 92.7 |
|  | SD | 28.8 |

| | Day 3 | | Day 6 | | Day 9 | | Day 12 | | Day 15 | |
| --- | --- | --- | --- | --- | --- | --- | --- | --- | --- | --- |
| % smaller | bead/bag | with tegaderm | bead/bag | with tegaderm | bead/bag | with tegaderm | bead/bag | with tegaderm | bead/bag | with tegaderm |
| TET OFF | | | | | | | | | | |
| mean | 13.2 | 0 | 34.2 | 2.2 | 74.4 | 52.4 | 84.6 | 81.2 | 99 | 98.6 |
| Std Dev | 17.5 | 0 | 14.5 | 4.3 | 10.9 | 21.1 | 10.5 | 13.8 | 2.2 | 3.1 |
| significance | | | $p < 0.002$ | | $p < 0.07$ | | | | | |
| TET ON | | | | | | | | | | |
| mean | 7.2 | 70 | 25.4 | 84.6 | 65.2 | 97.8 | 92.2 | 100 | 100 | 100 |
| Std Dev | 10.2 | 7.2 | 15.9 | 11.9 | 20.5 | 2.6 | 6.8 | 0 | 0 | 0 |
| significance | $p < 0.000$ | | $p < 0.000$ | | $p < 0.02$ | | $p < 0.05$ | | | |

| significance: | | |
| --- | --- | --- |
| | Day 3 teg mice vs tet on teg mice | $p < 0.000$ |
| | Day 6 teg mice vs tet on teg mice | $p < 0.000$ |
| | Day 9 teg mice vs tet on teg mice | $p < 0.004$ |

TABLE 3

| well ID | OD value | Result | Sample Volume | Factor (200 uL TV) | EGF (pg/mL) | Sample ID | TET status |
|---|---|---|---|---|---|---|---|
| | | | | | | Sept 26 Day 1 | |
| A1 | −0.004 | 0 | 25 | | | 6 | off |
| A2 | −0.005 | 0 | 40 | | | 7 | |
| A3 | −0.005 | 0 | 30 | | | 8 | |
| A4 | −0.006 | 0 | 25 | | | 9 | |
| A5 | −0.004 | 0 | 25 | | | 10 | |
| A6 | −0.003 | 0 | 5 | | | 16 | ON |
| A7 | −0.002 | 0 | 20 | | | 17 | |
| A8 | 0.003 | 15.18 | 25 | 8 | 121.44 | 18 | |
| A9 | 0.001 | 11.24 | 50 | 4 | 44.96 | 19 | |
| A10 | 0.005 | 19.03 | 50 | 4 | 76.12 | 20 | |
| | | | | | | Sept 29 Day 4 | |
| A11 | 0 | 9.23 | 50 | 4 | 36.92 | 6 | Off |
| A12 | −0.003 | 0 | 20 | | | 7 | |
| B1 | −0.008 | 0 | 30 | | | 8 | |
| B2 | 0.405 | 1081.45 | 20 | 10 | 10814.5 | 17 | ON |
| B3 | 0.057 | 112.87 | 20 | 10 | 1128.7 | 18 | |
| B4 | 0.19 | 380.92 | 20 | 10 | 3809.2 | 19 | |
| B5 | 0.167 | 329.18 | 20 | 10 | 3291.8 | 20 | |
| | | | | | | Oct 18 Day 1 | |
| B6 | −0.005 | 0 | 50 | | | 1 | off |
| B7 | −0.004 | 0 | 100 | | | 2 | |
| B8 | −0.005 | 0 | 100 | | | 3 | |
| B9 | −0.005 | 0 | 10 | | | 4 | |
| B10 | −0.003 | 0 | 100 | | | 5 | |
| B11 | 0.039 | 80.62 | 90 | 2.2 | 177.36 | 11 | ON |
| B12 | 0.203 | 411.48 | 200 | 0 | 411.48 | 12 | |
| C1 | 0.066 | 129.18 | 100 | 2 | 258.36 | 13 | |
| C2 | 0.384 | 987.3 | 200 | 0 | 987.3 | 14 | |
| C3 | 0.048 | 96.7 | 200 | 0 | 96.7 | 15 | |
| | | | | | | Oct 20 Day 3 | |
| C4 | −0.005 | 0 | 200 | | | 2 | off |
| C5 | −0.002 | 0 | 200 | | | 4 | |
| C6 | −0.002 | 0 | 50 | | | 11 | ON |
| C7 | 0.059 | 116.488 | 200 | 0 | 116.48 | 12 | |
| C8 | 0.082 | 158.59 | 200 | 0 | 158.59 | 13 | |
| C9 | 0.088 | 169.79 | 200 | 0 | 169.79 | 14 | |
| C10 | 0.026 | 57.42 | 200 | 0 | 57.42 | 15 | |

TABLE 4

| Wound Measurements | | | EGF Measurements | | |
|---|---|---|---|---|---|
| Sept 25 Day 0 | | | Sept 26 Day 1 | | |
| Wound size | TET Off | TET On | EGF (pg/mL) | Mouse | TET status |
| mean | 103.1 | 92.7 | 0 | 7 | off |
| SD | 15.8 | 28.8 | 0 | 8 | |
| | | | 0 | 9 | |
| | | | 0 | 10 | |
| | | | 0 | 16 | ON |
| | | | 0 | 17 | |
| | | | 121.44 | 18 | |
| | | | 44.96 | 19 | |
| | | | 76.12 | 20 | |
| Sept 28 Day 3 | | | Sept 29 Day 4 | | |
| % smaller | TET Off | TET On | EGF (pg/mL) | Mouse | TET status |
| mean | 0 | 70 | 36.92 | 6 | off |
| SD | 0 | 7.2 | 0 | 7 | |
| | | | 0 | 8 | |
| | | | 10814.5 | 17 | On |
| | | | 1128.7 | 18 | |
| | | | 3809.2 | 19 | |
| | | | 3291.8 | 20 | |

TABLE 4-continued

| Wound Measurements | | | EGF Measurements |
|---|---|---|---|
| Oct 1 Day 6 | | | |
| % smaller | TET Off | TET On | |
| mean | 2.2 | 84.6 | |
| SD | 4.3 | 11.9 | |

As indicated by the data in Tables 2–4, the beads/bags showed a statistically significant difference in wound healing (i.e., a reduction in wound area) at day 2 compared to the bags alone (see Table 4, $p<0.027$). At day 4, the beads/bag (Table 2) treated mouse wounds had a significant reduction in wound area compared to the mouse wounds in the bags alone (Table 3), as indicated by the significance level ($p<0.008$) in Table 4. At day 6, there was no significant difference in wound healing between the two groups (see Table 3, $p<0.16$).

However, at day 8, there was again a statistically significant reduction in the wound area in the beads/bag group (Table 2) compared to the bags alone group (Table 3) (see Table 4, $p<0.05$).

The experiments of this example show that cultured human keratinocytes grown on a macroporous microcarriers (beads/bag) promote wound healing. The mouse model used is predicative that human keratinocytes grown on a macroporous microcarriers contained in bags will enhance wound healing in humans.

EXAMPLE 2

The experiments of this example demonstrate that human culture keratinocytes grown on macroporous microcarriers and contained in a porous enclosure that is then covered with a wound dressing material improve healing in surgically created wounds in mice.

A. Experimental Methodology

The experiments of this example were performed as described in Example 1, with the following exceptions. The group of mice that received the keratinocyte-coated CYTO-LINE 1™ macroporous microcarrier beads (Pharmacia Biotech) (i.e., the beads/bags group) comprised five animals, while the group that received only the bags (i.e., the bags only group) comprised four animals. (They are labelled 2 to 5 because Mouse 1 expired during anesthesia.) In this example the bags from both the beads/bags group and the bags only group were covered with a polyurethane film dressing (TEGADERM, 3M Health Care, St. Paul, Minn.) with a cellophane product.

More specifically, the wounds were dressed either with human cultured keratinocytes grown on beads (keratinocytes/beads) in a DELNET bag (P530 Natural; AET, Inc.) or a DELNET bag alone (P530 Natural; AET, Inc.). Thereafter, the bags were covered with a TEGADERM dressing which, in turn, was covered with a BANDAID (3M Healthcare). The bags were stapled to the mouse.

B. Experimental Results

Table 5 presents wound tissue area ($mm^2$) at baseline (day 0) and at days 2, 4, 6, and 8 for each mouse which received bags containing keratinocyte-coated beads (beads/bags); the reduction in size of the wound as a percentage of the original wound size for each mouse is also set forth. Analogous data for the mice that received bags alone is presented in Table 6.

Table 7 presents the cumulative data for i) the beads/bags mice and ii) the bags only mice.

TABLE 5

| | mouse 1 | | mouse 2 | | mouse 3 | | mouse 4 | | mouse 5 | |
|---|---|---|---|---|---|---|---|---|---|---|
| day | $mm^2$ | % smaller | $mm^2$ | % smaller | $mm^2$ | % smaller | $mm^2$ | % smaller | $mm^2$ | % smaller |
| cells with Elof bags | | | | | | | | | | |
| 0 | 109.78 | | 120.56 | | 124.67 | | 114.67 | | 134.44 | |
| 2 | 106.33 | 3.14 | 130 | 0.00 | 146.67 | 0.00 | 119.39 | 0.00 | 130.1 | 3.23 |
| 4 | 123.33 | 0.00 | 112.78 | 6.45 | 154 | 0.00 | 110.2 | 3.90 | 106.76 | 20.59 |
| 6 | 71.56 | 34.82 | 63.56 | 47.28 | 130.89 | 0.00 | 88.78 | 22.58 | 130.48 | 2.95 |
| 8 | 65.44 | 40.39 | 48 | 60.19 | 48.89 | 60.78 | 36.73 | 67.97 | 70.41 | 47.63 |
| 10 | 53.67 | 51.11 | 40 | 66.82 | 38 | 69.52 | 18.37 | 83.98 | 12.5 | 90.70 |
| 12 | 41.56 | 62.14 | 23.33 | 80.65 | 8 | 93.58 | 16.58 | 85.54 | 8.93 | 93.36 |

| | mouse 6 | | mouse 7 | | mouse 8 | | mouse 9 | | mouse 10 | |
|---|---|---|---|---|---|---|---|---|---|---|
| day | $mm^2$ | % smaller | $mm^2$ | % smaller | $mm^2$ | % smaller | $mm^2$ | % smaller | $mm^2$ | % smaller |
| cells with plastic wrap | | | | | | | | | | |
| 0 | 112.37 | | 121.28 | | 149.82 | | 109.63 | | 123.17 | |
| 2 | 119.86 | 0 | 83.23 | 31.37 | 147.44 | 1.59 | 127.83 | 0 | 127.27 | 0 |
| 4 | 83.23 | 25.93 | 73.84 | 39.12 | 91.32 | 39.05 | 138.48 | 0 | 86.77 | 29.55 |
| 6 | 89.89 | 20.01 | 52.32 | 56.86 | 84.78 | 43.41 | 85.44 | 22.07 | 115.85 | 5.94 |
| 8 | 34.24 | 69.53 | 18.31 | 84.90 | 32.34 | 78.41 | 47.94 | 56.27 | 31.07 | 74.77 |
| 10 | 17.12 | 84.76 | 15.7 | 87.05 | 18.31 | 87.78 | 26.63 | 75.71 | 11.65 | 90.54 |
| 12 | 15.22 | 86.46 | 9.51 | 92.16 | 0 | 100 | 0 | 100 | 0 | 100 |

| | mouse 11 | | mouse 12 | | mouse 13 | | mouse 14 | | mouse 15 | |
|---|---|---|---|---|---|---|---|---|---|---|
| day | $mm^2$ | % smaller | $mm^2$ | % smaller | $mm^2$ | % smaller | $mm^2$ | % smaller | $mm^2$ | % smaller |
| TET on cells with Elof bags | | | | | | | | | | |
| 0 | 124.14 | | 107.02 | | 143.76 | | 62.78 | | 90.25 | |
| 2 | 108.2 | 12.84 | 119.86 | 0.00 | 93.1 | 35.24 | 86.21 | 0 | 113.2 | 0 |
| 4 | 20.33 | 83.62 | 19.62 | 81.67 | 49.23 | 65.76 | 65.64 | 0 | 27.82 | 69.17 |
| 6 | 11.89 | 90.42 | 0 | 100 | 0 | 100 | 21.4 | 65.91 | 0 | 100 |
| 8 | 0 | 100 | 0 | 100 | 0 | 100 | 0 | 100 | 0 | 100 |
| 10 | 0 | 100 | 0 | 100 | 0 | 100 | 0 | 100 | 0 | 100 |
| 12 | 0 | 100 | 0 | 100 | 0 | 100 | 0 | 100 | 0 | 100 |

| | mouse 16 | | mouse 17 | | mouse 18 | | mouse 19 | | mouse 20 | |
|---|---|---|---|---|---|---|---|---|---|---|
| day | $mm^2$ | % smaller | $mm^2$ | % smaller | $mm^2$ | % smaller | $mm^2$ | % smaller | $mm^2$ | % smaller |
| TET on cells with plastic wrap | | | | | | | | | | |
| 0 | 110 | | 148 | | 117.11 | | 139.33 | | 152.11 | |
| 2 | 138 | 0 | 124.67 | 15.76 | 105.78 | 9.67 | 122.67 | 11.96 | 138.67 | 8.84 |
| 4 | 72 | 34.55 | 44.44 | 69.97 | 101.33 | 13.47 | 80 | 42.58 | 84.33 | 44.56 |

TABLE 5-continued

| 6  | 0 | 100 | 13.33 | 90.99 | 11.56 | 90.13 | 19 | 86.36 | 31.11 | 79.55 |
|----|---|-----|-------|-------|-------|-------|----|-------|-------|-------|
| 8  | 0 | 100 | 5.33  | 96.40 | 6.22  | 94.69 | 0  | 100   | 19.56 | 87.14 |
| 10 | 0 | 100 | 3.33  | 97.75 | 5.44  | 95.35 | 0  | 100   | 39    | 74.36 |
| 12 | 0 | 100 | 0     | 100   | 0     | 100   | 0  | 100   | 10    | 93.43 |

TABLE 6

| % smaller | Day 2 | | Day 4 | | Day 6 | | Day 8 | | Day 10 | | Day 12 | |
|---|---|---|---|---|---|---|---|---|---|---|---|---|
| | TET Off | TET On | TET Off | TET On | TET Off | TET On | TET Off | TET On | TET Off | TET On | TET Off | TET On |
| Cells with Elof's bag | | | | | | | | | | | | |
| mean | 1.2 | 9.6 | 6.1 | 60 | 21.52 | 91.2 | 55.3 | 100 | 72.4 | 100 | 83 | 100 |
| Std Dev | 1.7 | 15.3 | 8.5 | 34.4 | 20.3 | 14.7 | 11.1 | 0 | 15.5 | 0 | 12.9 | 0 |
| significance | | | $p = 0.004$ | | $p < 0.001$ | | $p = 0.014$ | | $p = 0.010$ | | $p = 0.008$ | |
| Cells with Plastic Wrap | | | | | | | | | | | | |
| mean | 6.5 | 9.2 | 26.7 | 41 | 29.6 | 89.4 | 72.7 | 77.6 | 85.1 | 93.4 | 95.7 | 98.6 |
| Std Dev | 13.8 | 5.8 | 16 | 20.3 | 20.2 | 7.4 | 10.7 | 38 | 5.6 | 10.8 | 6.1 | 2.9 |
| significance | | | | | $p < 0.001$ | | | | | | | |

| Day 0 size (mm²) | | | |
|---|---|---|---|
| cells with Elof bag | | mean | 120.8 |
| | | SD | 9.4 |
| cells with plastic wrap | | mean | 123.2 |
| | | SD | 15.9 |
| TET ON with Elof bag | | mean | 105.5 |
| | | SD | 31.1 |
| TET ON with plastic wrap | | mean | 133.3 |
| | | SD | 18.7 |

TABLE 7

| Wound Measurements | | | EGF Measurements | | |
|---|---|---|---|---|---|
| Oct 17 Day 0 | | | Oct 18 Day 1 | | |
| Wound Size | TET Off | TET On | EGF (pg/mL) | Mouse | TET status |
| mean | 120.8 | 105.5 | 0 | 1 | off |
| SD | 9.4 | 31.1 | 0 | 2 | |
| | | | 0 | 3 | |
| | | | 0 | 4 | |
| | | | 0 | 5 | |
| | | | 177.36 | 11 | ON |
| | | | 411.48 | 12 | |
| | | | 258.36 | 13 | |
| | | | 987.3 | 14 | |
| | | | 96.7 | 15 | |
| Oct 19 Day 2 | | | Oct 20 Day 3 | | |
| % smaller | TET Off | TET On | EGF (pg/mL) | Mouse | TET status |
| mean | 1.2 | 9.6 | 0 | 2 | off |
| Std Dev | 1.7 | 15.3 | 0 | 4 | |
| | | | 0 | 11 | ON |
| | | | 116.48 | 12 | |
| | | | 158.59 | 13 | |
| | | | 169.79 | 14 | |
| | | | 57.42 | 15 | |
| Oct 21 Day 4 | | | | | |
| % smaller | TET Off | TET On | | | |
| mean | 6.1 | 60 | | | |
| Std Dev | 8.5 | 34.4 | | | |

As indicated by the data in Tables 5–7, the beads/bags demonstrated a statistically significant difference in wound healing (i.e., a reduction in wound area) at day 4 compared to the bags alone (see Table 7, p<0.026). The statistically significant difference in wound healing between the two groups was maintained on days 6 and 8 (p<0.010 and p<0.030, respectively).

Comparison of the data in Table 7 to that in Table 4 (Example 1) indicates that the wound dressings without TEGADERM begin to contract earlier than those with TEGADERM. More specifically, the wounds of the beads/bags animals treated without TEGADERM were 12.7% smaller by day 2 and 33.9% smaller by day 4, while the wounds of the beads/bags animals treated with TEGADERM were 2.2% and 18.8% smaller on the same days. However, the size of the wounds of the beads/bags animals treated with TEGADERM became smaller than those treated without TEGADERM on days 6 and 8. While an understanding of the mechanism for this effect is not required in order to practice the present invention, it is believed to be due, in part, to the ability of the TEGADERM to keep the wounds moist.

The experiments of this example indicate that the systems and methods of the present invention can be practiced in combination with conventional wound healing means and procedures.

Based upon the preceding discussion and experimental materials, it should be clear that the present invention provides effective and efficient systems and methods for wound healing, especially healing of chronic wounds. The devices and methods may be used alone or in combination with other means traditionally employed in wound healing.

EXAMPLE 3

The experiments of this example demonstrate that a tetr-expressing cell line transfected with hEFG and grown on macroporous microcarriers and contained in a porous enclosure, improves healing in surgically created wounds in mice.

A. Experimental Methodology

Cells

Osteosarcoma line U20S were grown and maintained in Dulbecco's modified Eagle's medium (DMEM) supplemented with 10% fetal bovine serum. The tetR—expressing cell line, U2CEP4R-11, was cotransfected with pcDNA3, pcmvtetOEGF and EcoRI-linearized pcmvtetOEGF to establish cell lines that expressed tetR and HEGF. Medium containing hygromycin B and G418 was used to select cells resistant to hygromycin B. The HEGF-expressing cell lines were determined by analysis of hEGF expression in the presence or absence of tetracycline. [See, Yao et al., *Hum Gene Ther*. Feb. 10, 1999;10(3):419–27; and Yao et al., *Hum Gene Ther*. Sep. 1, 1998;9(13):1939–50].

Cytoline 1™ Bead Wash

Five grams of CYTOLINE 1 macroporous microcarrier beads (Pharmacia Biotech) were autoclaved for 10 minutes in 40 mL Milli Q water (Millipore, Bedford, Mass.) in a 125 mL Erlenmeyer flask. Following the autoclaving procedure, the beads were cooled and the water was aspirated. The beads were re-suspended in 40 mL Milli Q water, and were agitated at moderate speed on a Labline orbital shaker for 10 minutes.

The water was again aspirated, and a final washing with 40 mL Milli Q water was performed. The beads were transferred into a 50 mL conical culture tube, the water was aspirated, and 30 mL 0.1 N NaOH was added. The beads were incubated at room temperature overnight. The NaOH was aspirated off the beads, and the beads were resuspended in 50 mL Milli Q water. The aliquot was transferred to a 125 Erlemneyer flask and shaken at moderate speed for ten minutes. The Milli Q water was aspirated off the beads, and the beads were resuspended in Milli Q water; this aspiration/resuspension procedure was repeated a total of five times. The pH was checked until neutral (i.e., less that 8), as measured with pH paper.

The beads were aspirated and resuspended in 40 mL PBS without $Mg^{2+}$ and $Ca^{2+}$, and autoclaved 30 minutes at 121 C.

Growth of U20S Cell Line on Cytoline 1™ Beads

A slurry containing 10 mL of PBS solution and 5 grams of beads (contained in a 50 mL sterile conical centrifuge tube) was autoclaved as described above. The PBS was decanted, and 50 mL of DMEM medium was added to the beads. The cells were conditioned in the medium at 37 C with 5% $CO_2$ gas for 48 hours.

The medium was decanted, and the beads were transferred into a separate 50 ml sterile centrifuge tube. Ten-to-15 mL of medium was added, and the suspension was centrifuged at 1000 rpm for 3 minutes. The medium was again decanted, and $30 \times 10^6$ U20S transfected cells were added. After gently agitating for 5 minutes, the cells and beads were poured into a 250 mL glass roller bottle and 50 mL of medium was added; this was performed using a fermentor-agitated growth system.

As a toxicity assay, 5 mL of cells and beads were removed from the glass roller bottle and grown in a T-25 flask to determine the growth of the cells on the plastic bottom of the flask in the presence of the beads. The roller bottle was incubated overnight at 37 C, after which 100 mL additional medium was added to the roller bottle and the rotation of the roller bottle was initiated (rotation rate=one turn/15 seconds).

To feed the cells, an aliquot of medium was removed and replaced by fresh medium, adjusted to the correct pH with $CO_2$ gassing. The cells were fed every 48 hours.

Experimental Design

A fifteen-day animal trial was conducted with two groups of ten animals each. The wound dressings (see below) were changed every third day starting at day 0. Wound area measurements and photographs were obtained on days 0, 3, 6, 9, 12, and 15. Wound fluid collection occurred on days 1 and 4.

All surgical procedures were performed under sterile conditions inside a lamina flow hood. Five week old, male Nu/J mice (Jackson Labs) were used. Nu/J mice contain a recessive mutation found on chromosome 11 and are athymic (T-cell deficient). The mice have a reduced lymphocyte count comprised almost entirely of B-cells, a normal IgM response to thymus-independence antigens, a poor response thymus antigens, increased macrophage and NK cell activity, and increased susceptibility to infection. NU/J mice do not reject allogeneic and xenogeneic skin and tumor grafts. Wounds in these mice heal poorly.

The mice were anesthetized with metofane (Mallinckrodt Veterinary) and prepped with ethanol. Using fine surgical scissors, a full thickness surgical wound approximately 98 $mm^2$ in area was created on the backs of the mice. The wound dressings (see below) were secured in the cephalad end of the wound with a surgical staple. Thereafter, each mouse was returned to its biohazard containment cage.

On day 1 and 4, the animals were returned to the laminar flow hood, lightly restrained and wound fluid was aspirated. On days 3,6,9,12, and 15, the animals were returned to the laminar flow hood for removal of the staple and replacement of the bag. The animals were lightly restrained while area and photographic measurements were obtained (described below). The dressing was replaced and secured; all dressing changes were performed using sterile technique without general anesthesia.

Wound Dressing

The wounds were dressed either with U20S transfected cells grown on beads or U20S transfected cells grown on beads in the presence of 1 ug/mL tetracycline for 24 hours (tet on cells) before application. Both groups of cells and beads were enclosed in DELNET bags (P530 Natural; AET, Inc.) approximately 23 mm×25 mm. The seams of the bags were prepared with an Impulse heat-sealing unit (American International Electric Co.). Prior to filling and application on the mice, the DELNET bags were gas sterilized with ethylene oxide and placed in a sterile package. TEGADERM (3M Healthcare) covered the DELNET bags, a BANDAID (3M Healthcare) covered both and was secured with surgical staples (Richard-Allen, Inc.) in half of the mice. The TEGADERM adhered to the skin of the mouse, the bag and the BANDAID were stapled to the mouse. The remaining mice did not have TEGADERM covering the bag and wound.

The bag and bead assembly was performed in a tissue culture hood. Inside the laminar flow hood, the U20S/bead suspensions were transferred to the DELNET bag with a sterile glass pipet. Approximately 250 µL of the U20S/bead suspension (with or without tetracycline exposure) was placed in the bag. After the beads were loaded into the bag, the final seam was made with an Impulse heat-sealer. The DELNET bag containing the U20S/bead suspension was referred to as "TET-Off cells," while the DELNET bag with the suspension that was incubated 24 hours with tetracycline is referred to as "TET-On cells." The TET-Off cells were place in DMEM medium while the TET-On cells were place in DMEM medium with 1 µL/mL tetracycline after they were loaded and heat-sealed.

Measurement of Wound Area

Total area of mouse wounds was performed as previously described [Schwarz et al., *Wound Repair and Regeneration*, 3:204–212 (1995)]. Briefly, the area of the wound was traced on transparency film (Apollo, Ronkonkoma, N.Y.) with an ultra fine tip marker. The transparency film was photocopied onto plain paper and subsequently scanned into a bitmap file using the HP ScanJet 4c (Hewlett Packard, Boise, Id.). Tissue area was calculated with non-rectangular area analysis used by ImagePC (Scion Corp., Frederick, Md.) and the data was expressed as millimeters squared. Mean and standard deviation were calculated using SigmaStat software (SPSS Inc., Chicago, Ill.). A statistically significant difference was considered as $p<0.05$.

Measurement of EGF Concentration

Wound fluid was collected 24 hours after the bead bag dressing was applied. Sterile saline (200 µL) was injected into the wound dressing to facilitate in collecting any fluid that had collected overnight. A syringe with a 24 gauge needle was used to collect the wound fluid. The wound fluid was frozen in liquid nitrogen and stored until time of analysis.

The wells of a 96 well titer plate was coated with 125 ng of anti-EGF monoclonal antibody. The wound fluid was added to the wells and adjusted to 200 µL (total volume) with growth medium. The reaction was carried out at 4 C for 18 hours. The plate was then washed with PBS then 75 ng of anti-EGF polyclonal antibody was added and incubated for 3 hours. The plate was washed again with PBS, 1:3000 dilution of HRP-Goat anti-rabbit antibody was added and incubated for 1.5 hours. The plate was washed with PBS then the Bio-Rad HRP assay was run.

B. Experimental Results

Table 8 presents wound tissue area ($mm^2$) at baseline (day 0) and at days 3, 6, 9, 12, and 15 for each mouse that received bags containing U20S transfected cells (TET Off cells) and U20S transfected cells exposed to tetracycline (TET-On cells); the reduction in size of the wound as a percentage of the original wound size for each mouse is also set forth. Table 9 presents the cumulative data for i) the TET-Off mice and ii) the TET-On mice.

TABLE 8

| Day | mouse 1 $mm^2$ | % smaller | mouse 2 $mm^2$ | % smaller | mouse 3 $mm^2$ | % smaller | mouse 4 $mm^2$ | % smaller | mouse 5 $mm^2$ | % smaller |
|---|---|---|---|---|---|---|---|---|---|---|
| | | | | | Cells/Beads Only | | | | | |
| 0 | 72.33 | | 68 | | 128 | | 113.33 | | 113.33 | |
| 3 | 84.44 | 0 | 63.56 | 7 | 105.78 | 17 | 65.44 | 42 | 65.44 | 0 |
| 6 | 63.89 | 12 | 42.67 | 37 | 88 | 31 | 54 | 52 | 54 | 39 |
| 9 | 17.33 | 76 | 13 | 81 | 31.78 | 75 | 18 | 84 | 18 | 56 |
| 12 | 24.89 | 66 | 6 | 91 | 17.78 | 86 | 10 | 91 | 10 | 89 |
| 15 | 3.89 | 95 | 0 | 100 | 0 | 100 | 0 | 100 | 0 | 100 |

| ID (day) | mouse 6 $mm^2$ | % smaller | mouse 7 $mm^2$ | % smaller | mouse 8 $mm^2$ | % smaller | mouse 9 $mm^2$ | % smaller | mouse 10 $mm^2$ | % smaller |
|---|---|---|---|---|---|---|---|---|---|---|
| | | | | | Cells/Beads with Tegaderm | | | | | |
| 0 | 109.56 | | 108.63 | | 78 | | 99.56 | | 120 | |
| 3 | 159 | 0 | 145 | 0 | 156.44 | 0 | 177.22 | 0 | 133.78 | 0 |
| 6 | 122.67 | 0 | 116 | 0 | 77 | 1 | 136.89 | 0 | 107.56 | 10 |
| 9 | 38.89 | 65 | 39.11 | 64 | 45 | 42 | 80 | 20 | 35 | 71 |
| 12 | 36.67 | 67 | 32.11 | 70 | 8 | 90 | 20.44 | 79 | 0 | 100 |
| 15 | 7.78 | 93 | 0 | 100 | 0 | 100 | 0 | 100 | 0 | 100 |

| ID (day) | mouse 11 $mm^2$ | % smaller | mouse 12 $mm^2$ | % smaller | mouse 13 $mm^2$ | % smaller | mouse 14 $mm^2$ | % smaller | mouse 15 $mm^2$ | % smaller |
|---|---|---|---|---|---|---|---|---|---|---|
| | | | | | TET "on" Cells/Beads | | | | | |
| 0 | 66.58 | | 159.18 | | 95.66 | | 70.89 | | 61.11 | |
| 3 | 114.41 | 0 | 172.58 | 0 | 75 | 22 | 86.33 | 0 | 52.78 | 14 |
| 6 | 81.38 | 0 | 94.9 | 40 | 65.43 | 32 | 46.22 | 35 | 48.89 | 20 |
| 9 | 15.31 | 77 | 47.7 | 70 | 19.64 | 79 | 20.78 | 71 | 43.44 | 29 |
| 12 | 0 | 100 | 23.85 | 85 | 3.83 | 96 | 10.67 | 85 | 3.33 | 95 |
| 15 | 0 | 100 | 0 | 100 | 0 | 100 | 0 | 100 | 0 | 100 |

TABLE 8-continued

| ID | mouse 16 | | mouse 17 | | mouse 18 | | mouse 19 | | mouse 20 | |
|---|---|---|---|---|---|---|---|---|---|---|
| (day) | mm² | % smaller | mm² | % smaller | mm² | % smaller | mm² | % smaller | mm² | % smaller |
| TET "on" Cells/Beads with Tegaderm | | | | | | | | | | |
| 0 | 68.88 | | 89.29 | | 134.44 | | 64.44 | | 106.78 | |
| 3 | 26.79 | 61 | 30.61 | 66 | 26.53 | 80 | 17.11 | 73 | 22.44 | 79 |
| 6 | 11.48 | 83 | 31.51 | 65 | 12.5 | 91 | 7.78 | 88 | 3.89 | 96 |
| 9 | 2.68 | 96 | | died | 6.25 | 95 | 0 | 100 | 0 | 100 |
| 12 | 0 | 100 | | | 0 | 100 | 0 | 100 | 0 | 100 |
| 15 | 0 | 100 | | | 0 | 100 | 0 | 100 | 0 | 100 |

TABLE 9

| Day 0 size (mm²) | | | |
|---|---|---|---|
| cells/bag | | mean | 106.1 |
| | | SD | 35.3 |
| cells/bag tegaderm | | mean | 103.1 |
| | | SD | 15.8 |
| tet cells/bag | | mean | 90.7 |
| | | SD | 40.5 |
| tet cells/bag tegaderm | | mean | 92.7 |
| | | SD | 28.8 |

| | Day 3 | | Day 6 | | Day 9 | | Day 12 | | Day 15 | |
|---|---|---|---|---|---|---|---|---|---|---|
| % smaller | bead/bag | with tegaderm | bead/bag | with tegaderm | bead/bag | with tegaderm | bead/bag | with tegaderm | bead/bag | with tegaderm |
| TET OFF | | | | | | | | | | |
| mean | 13.2 | 0 | 34.2 | 2.2 | 74.4 | 52.4 | 84.6 | 81.2 | 99 | 98.6 |
| Std Dev | 17.5 | 0 | 14.5 | 4.3 | 10.9 | 21.1 | 10.5 | 13.8 | 2.2 | 3.1 |
| significance | | | $p < 0.002$ | | $p < 0.07$ | | | | | |
| TET ON | | | | | | | | | | |
| mean | 7.2 | 70 | 25.4 | 84.6 | 65.2 | 97.8 | 92.2 | 100 | 100 | 100 |
| Std Dev | 10.2 | 7.2 | 15.9 | 11.9 | 20.5 | 2.6 | 6.8 | 0 | 0 | 0 |
| significance | $p < 0.000$ | | $p < 0.000$ | | $p < 0.02$ | | $p < 0.05$ | | | |

| significance: | | |
|---|---|---|
| | Day 3 teg mice vs tet on teg mice | $p < 0.000$ |
| | Day 6 teg mice vs tet on teg mice | $p < 0.000$ |
| | Day 9 teg mice vs tet on teg mice | $p < 0.004$ |

As indicated by the data in Tables 8–9, the TET-On cells with TEGADERM showed a statistically significant difference in wound healing (i.e., a reduction in wound area) at day 3 compared to TET-Off cells (see Table 9, p<0.001). At day 6, the TET-On cells with TEGADERM treated mouse wounds had a significant reduction in wound area compared to the TET-Off cells (Table 8), as indicated by the significance level p<0.001 in Table 9. At day 9, there was no significance in wound healing between the two groups (see Table 9, p<0.02). However, at day 12, there was again a statistically significant reduction in wound area in the TET-On group compared to the TET-Off group (Table 8) (see Table 9, p<0.05).

The experiments of this example show the U20S transfected cells, exposed to tetracycline, grown on macroporous microcarriers (TET-On cells) promote wound healing. The mouse model is predicative that TET-On transfected cells grown on macroporous microcarriers contained in bags will enhance wound healing in humans. Optimal conditions for this experiment to work was a consistently moist environment.

Table 10 shows the values of EGF that were in the wound fluid on day 1 and day 4. These results were obtain 24 hours after application of the dressings. EGF was measurable in cells that had been treated with tetracycline (TET-On cells) while none was detectable in the non-treated cells (TET-Off cells). Table 11 show the EGF results compared to the wound size over five days.

TABLE 10

| well ID | OD value | Result | Sample Volume | Factor (200 uL TV) | EGF (pg/mL) | Sample ID | TET status |
|---|---|---|---|---|---|---|---|
| | | | | | | Sept 26 Day 1 | |
| A1 | −0.004 | 0 | 25 | | | 6 | off |
| A2 | −0.005 | 0 | 40 | | | 7 | |

TABLE 10-continued

| well ID | OD value | Result | Sample Volume | Factor (200 uL TV) | EGF (pg/mL) | Sample ID | TET status |
|---|---|---|---|---|---|---|---|
| A3 | −0.005 | 0 | 30 | | | 8 | |
| A4 | −0.006 | 0 | 25 | | | 9 | |
| A5 | −0.004 | 0 | 25 | | | 10 | |
| A6 | −0.003 | 0 | 5 | | | 16 | ON |
| A7 | −0.002 | 0 | 20 | | | 17 | |
| A8 | 0.003 | 15.18 | 25 | 8 | 121.44 | 18 | |
| A9 | 0.001 | 11.24 | 50 | 4 | 44.96 | 19 | |
| A10 | 0.005 | 19.03 | 50 | 4 | 76.12 | 20 | |
| A11 | 0 | 9.23 | 50 | 4 | 36.92 | 6 | off |
| A12 | −0.003 | 0 | 20 | | | 7 | |
| B1 | −0.008 | 0 | 30 | | | 8 | |
| B2 | 0.405 | 1081.45 | 20 | 10 | 10814.5 | 17 | ON |
| B3 | 0.057 | 112.87 | 20 | 10 | 1128.7 | 18 | |
| B4 | 0.19 | 380.92 | 20 | 10 | 3809.2 | 19 | |
| B5 | 0.167 | 329.18 | 20 | 10 | 3291.8 | 20 | |
| | | | | | | Oct 18 Day 1 | |
| B6 | −0.005 | 0 | 50 | | | 1 | off |
| B7 | −0.004 | 0 | 100 | | | 2 | |
| B8 | −0.005 | 0 | 100 | | | 3 | |
| B9 | −0.005 | 0 | 10 | | | 4 | |
| B10 | −0.003 | 0 | 100 | | | 5 | |
| B11 | 0.039 | 80.62 | 90 | 2.2 | 177.36 | 11 | ON |
| B12 | 0.203 | 411.48 | 200 | 0 | 411.48 | 12 | |
| C1 | 0.066 | 129.18 | 100 | 2 | 258.36 | 13 | |
| C2 | 0.384 | 987.3 | 200 | 0 | 987.3 | 14 | |
| C3 | 0.048 | 96.7 | 200 | 0 | 96.7 | 15 | |
| | | | | | | Oct 20 Day 3 | |
| C4 | −0.005 | 0 | 200 | | | 2 | off |
| C5 | −0.002 | 0 | 200 | | | 4 | |
| C6 | −0.002 | 0 | 50 | | | 11 | ON |
| C7 | 0.059 | 116.488 | 200 | 0 | 116.48 | 12 | |
| C8 | 0.082 | 158.59 | 200 | 0 | 158.59 | 13 | |
| C9 | 0.088 | 169.79 | 200 | 0 | 169.79 | 14 | |
| C10 | 0.026 | 57.42 | 200 | 0 | 57.42 | 15 | |

TABLE 11

| Wound Measurements | | | EGF Measurements | | |
|---|---|---|---|---|---|
| Sept 25 Day 0 | | | Sept 26 Day 1 | | |
| Wound size | TET Off | TET On | EGF (pg/mL) | Mouse | TET status |
| mean | 103.1 | 92.7 | 0 | 7 | off |
| SD | 15.8 | 28.8 | 0 | 8 | |
| | | | 0 | 9 | |
| | | | 0 | 10 | |
| | | | 0 | 16 | ON |
| | | | 0 | 17 | |
| | | | 121.44 | 18 | |
| | | | 44.96 | 19 | |
| | | | 76.12 | 20 | |
| Sept 28 Day 3 | | | Sept 29 Day 4 | | |
| % smaller | TET Off | TET On | EGF (pg/mL) | Mouse | TET status |
| mean | 0 | 70 | 36.92 | 6 | off |
| SD | 0 | 7.2 | 0 | 7 | |
| | | | 0 | 8 | |
| | | | 10814.5 | 17 | On |
| | | | 1128.7 | 18 | |
| | | | 3809.2 | 19 | |
| | | | 3291.8 | 20 | |
| Oct 1 Day 6 | | | | | |
| % smaller | TET Off | TET On | | | |
| mean | 2.2 | 84.6 | | | |
| SD | 4.3 | 11.9 | | | |

Although expression of EGF was under regulatory control by tet, it will be appreciated that any regulatory system (or nonregulatory system) may be employed. In addition, physical removal of the enclosure may also be used to "regulate" the amount of cell factors or proteins of interest delivered to a target site.

EXAMPLE 4

The experiments of this example demonstrated that tet-R expressing cell line transfected with HEGF and grown on macroporous microcarrier and contained in a porous enclosure improves healing in surgically created wound in mice.

A. Experimental Methodology

The experiments of this example were performed as described in Example 3 with the following exceptions. This was a 12-day animal trial with two groups of ten animals each. The wound dressing was changed every other day starting on day 0. Wound measurements were obtained days 8, 10, and 12. Wound fluid collection occurred on days 1 and 3. Ten of the mice had their bead/cell bag covered wound enclosed in an occlusive collection system as described in U.S. Pat. No. 5,152,757 (hereby incorporated by reference). The remaining 10 mice bead/cell bag covered wounds were enclosed with plastic film (Dow Chemical Co.).

More specifically, the wounds were dressed with either an occlusive collection system or plastic film to provide better wound healing conditions as shown in Example 3. Covering the wounds in this manner also facilitated in the collection of wound fluid for EGF determinations. The wounds were covered with the bead/bag then the collection system was adhered to the back of the mice and stapled to the skin. A BAND AID adhesive bandage was used to adhere the plastic film to the back of the mice and stapled as in Example 3.

B. Experimental Results

Table 12 presents wound tissue area (mm$^2$) at baseline (day 0) and at days 2, 4, 6, 8, 10, and 12 for each mouse that received bags containing U20S transfected cells (TET-Off cells) and U20S transfected cells exposed to tetracycline (TET-On cells); the reduction in size of the wound as a percentage of the original wound size for each mouse is also set forth. Table 13 presents the cumulative data for i) the TET-Off mice and ii) the TET On mice.

TABLE 12

| | | mouse 1 | | mouse 2 | | mouse 3 | | mouse 4 | | mouse 5 | |
|---|---|---|---|---|---|---|---|---|---|---|---|
| | day | mm$^2$ | % smaller | mm$^2$ | % smaller | mm$^2$ | % smaller | mm | % smaller | mm$^2$ | % smaller |
| | | | | | | Cells with Elof bags | | | | | |
| | 0 | 109.78 | | 120.56 | | 124.67 | | 114.67 | | 134.44 | |
| | 2 | 106.33 | 3.14 | 130 | 0.00 | 146.67 | 0.00 | 119.39 | 0.00 | 130.1 | 3.23 |
| | 4 | 123.33 | 0.00 | 112.78 | 6.45 | 154 | 0.00 | 110.2 | 3.90 | 106.76 | 20.59 |
| | 6 | 71.56 | 34.82 | 63.56 | 47.28 | 130.89 | 0.00 | 88.78 | 22.58 | 130.48 | 2.95 |
| | 8 | 65.44 | 40.39 | 48 | 60.19 | 48.89 | 60.78 | 36.73 | 67.97 | 70.41 | 47.63 |
| | 10 | 53.67 | 51.11 | 40 | 66.82 | 38 | 69.52 | 18.37 | 83.98 | 12.5 | 90.70 |
| | 12 | 41.56 | 62.14 | 23.33 | 80.65 | 8 | 93.58 | 16.58 | 85.54 | 8.93 | 93.36 |
| | | mouse 6 | | mouse 7 | | mouse 8 | | mouse 9 | | mouse 10 | |
| | day | mm$^2$ | % smaller | mm$^2$ | % smaller | mm$^2$ | % smaller | mm$^2$ | % smaller | mm$^2$ | % smaller |
| | | | | | | Cells with plastic wrap | | | | | |
| | 0 | 112.37 | | 121.28 | | 149.82 | | 109.63 | | 123.17 | |
| | 2 | 119.86 | 0 | 83.23 | 31.37 | 147.44 | 1.59 | 127.83 | 0 | 127.27 | 0 |
| | 4 | 83.23 | 25.93 | 73.84 | 39.12 | 91.32 | 39.05 | 138.48 | 0 | 86.77 | 29.55 |
| | 6 | 89.89 | 20.01 | 52.32 | 56.86 | 84.78 | 43.41 | 85.44 | 22.07 | 115.85 | 5.94 |
| | 8 | 34.24 | 69.53 | 18.31 | 84.90 | 32.34 | 78.41 | 47.94 | 56.27 | 31.07 | 74.77 |
| | 10 | 17.12 | 84.76 | 15.7 | 87.05 | 18.31 | 87.78 | 26.63 | 75.71 | 11.65 | 90.54 |
| | 12 | 15.22 | 86.46 | 9.51 | 92.16 | 0 | 100 | 0 | 100 | 0 | 100 |
| | | mouse 11 | | mouse 12 | | mouse 13 | | mouse 14 | | mouse 15 | |
| | day | mm$^2$ | % smaller | mm$^2$ | % smaller | mm$^2$ | % smaller | mm$^2$ | % smaller | mm$^2$ | % smaller |
| | | | | | | TET on cells with Elof bags | | | | | |
| | 0 | 124.14 | | 107.02 | | 143.76 | | 62.78 | | 90.25 | |
| | 2 | 108.2 | 12.84 | 119.86 | 0.00 | 93.1 | 35.24 | 86.21 | 0 | 113.2 | 0 |
| | 4 | 20.33 | 83.62 | 19.62 | 81.67 | 49.23 | 65.76 | 65.64 | 0 | 27.82 | 69.17 |
| | 6 | 11.89 | 90.42 | 0 | 100 | 0 | 100 | 21.4 | 65.91 | 0 | 100 |
| | 8 | 0 | 100 | 0 | 100 | 0 | 100 | 0 | 100 | 0 | 100 |
| | 10 | 0 | 100 | 0 | 100 | 0 | 100 | 0 | 100 | 0 | 100 |
| | 12 | 0 | 100 | 0 | 100 | 0 | 100 | 0 | 100 | 0 | 100 |
| | | mouse 16 | | mouse 17 | | mouse 18 | | mouse 19 | | mouse 20 | |
| | day | mm$^2$ | % smaller | mm$^2$ | % smaller | mm$^2$ | % smaller | mm$^2$ | % smaller | mm$^2$ | % smaller |
| | | | | | | TET on cells with plastic wrap | | | | | |
| | 0 | 110 | | 148 | | 117.11 | | 139.33 | | 152.11 | |
| | 2 | 138 | 0 | 124.67 | 15.76 | 105.78 | 9.67 | 122.67 | 11.96 | 138.67 | 8.84 |
| | 4 | 72 | 34.55 | 44.44 | 69.97 | 101.33 | 13.47 | 80 | 42.58 | 84.33 | 44.56 |
| | 6 | 0 | 100 | 13.33 | 90.99 | 11.56 | 90.13 | 19 | 86.36 | 31.11 | 79.55 |
| | 8 | 0 | 100 | 5.33 | 96.40 | 6.22 | 94.69 | 0 | 100 | 19.56 | 87.14 |
| | 10 | 0 | 100 | 3.33 | 97.75 | 5.44 | 95.35 | 0 | 100 | 39 | 74.36 |
| | 12 | 0 | 100 | 0 | 100 | 0 | 100 | 0 | 100 | 10 | 93.43 |

TABLE 13

| | Day 2 | | Day 4 | | Day 6 | | Day 8 | | Day 10 | | Day 12 | |
|---|---|---|---|---|---|---|---|---|---|---|---|---|
| % smaller | TET Off | TET On | TET Off | TET On | TET Off | TET On | TET Off | TET On | TET Off | TET On | TET Off | TET On |
| | | | | | Cells with Elof's bag | | | | | | | |
| mean | 1.2 | 9.6 | 6.1 | 60 | 21.52 | 91.2 | 55.3 | 100 | 72.4 | 100 | 83 | 100 |
| Std Dev | 1.7 | 15.3 | 8.5 | 34.4 | 20.3 | 14.7 | 11.1 | 0 | 15.5 | 0 | 12.9 | 0 |
| significance | | | p = 0.004 | | p < 0.001 | | p = 0.014 | | p = 0.010 | | p = 0.008 | |

TABLE 13-continued

| | | | | | Cells with Plastic Wrap | | | | | | |
|---|---|---|---|---|---|---|---|---|---|---|---|
| mean | 6.5 | 9.2 | 26.7 | 41 | 29.6 | 89.4 | 72.7 | 77.6 | 85.1 | 93.4 | 95.7 | 98.6 |
| Std Dev | 13.8 | 5.8 | 16 | 20.3 | 20.2 | 7.4 | 10.7 | 38 | 5.6 | 10.8 | 6.1 | 2.9 |
| significance | | | | | $p < 0.001$ | | | | | | | |

| Day 0 size (mm$^2$) | | |
|---|---|---|
| cells with Elof bag | mean | 120.8 |
| | SD | 9.4 |
| cells with plastic wrap | mean | 123.2 |
| | SD | 15.9 |
| TET ON with Elof bag | mean | 105.5 |
| | SD | 31.1 |
| TET ON with plastic wrap | mean | 133.3 |
| | SD | 18.7 |

As indicated by the data in Tables 12 and 13, the TET-On cells with the occlusive collection system showed a statistically significant difference in wound healing (i.e., a reduction in wound area) at day 4 compared to the TET-Off cells (see Table 13, p=0.004). At days 6, 8, 10, and 12, the data still showed significance difference in wound healing compared to the TET-Off cells (see Table 13, p<0.014).

The experiments of this example show the U20S transfected cells, exposed to tetracycline, grown on macroporous microcarriers (TET-On cells) promote wound healing. The mouse model is predicative that TET-On transfected cells grown on macroporous microcarriers contained in bags will enhance wound healing in humans.

Table 10 shows the values of EGF that were in the wound fluid on day 1 and day 3. These results were obtain 24 hours after application of the dressings. EGF was measurable in cells that had been treated with tetracycline (TET-On cells) while none was detectable in the non-treated cells (TET-Off cells). Table 14 show the EGF results compared to the wound size over four days.

TABLE 14

| Wound Measurements | | | EGF Measurements | | |
|---|---|---|---|---|---|
| Oct 17 Day 0 | | | Oct 18 Day 1 | | |
| Wound Size | TET Off | TET On | EGF (pg/mL) | Mouse | TET status |
| mean | 120.8 | 105.5 | 0 | 1 | off |
| SD | 9.4 | 31.1 | 0 | 2 | |
| | | | 0 | 3 | |
| | | | 0 | 4 | |
| | | | 0 | 5 | |
| | | | 177.36 | 11 | ON |
| | | | 411.48 | 12 | |
| | | | 258.36 | 13 | |
| | | | 987.3 | 14 | |
| | | | 96.7 | 15 | |
| Oct 19 Day 2 | | | Oct 20 Day 3 | | |
| % smaller | TET Off | TET On | EGF pg/mL | Mouse | TET status |
| mean | 1.2 | 9.6 | 0 | 2 | off |
| Std Dev | 1.7 | 15.3 | 0 | 4 | |
| | | | 0 | 11 | ON |
| | | | 116.48 | 12 | |
| | | | 158.59 | 13 | |
| | | | 169.79 | 14 | |
| | | | 57.42 | 15 | |

TABLE 14-continued

| Wound Measurements | | | EGF Measurements |
|---|---|---|---|
| Oct 21 Day 4 | | | |
| % smaller | TET Off | TET On | |
| mean | 6.1 | 60 | |
| Std Dev | 8.5 | 34.4 | |

Based upon the preceding discussion and experimental materials, it should be clear that the present invention provides effective and efficient systems and methods for wound healing, especially healing of chronic wounds. The devices and methods may be used alone or in combination with other means traditionally employed in wound healing.

EXAMPLE 5

Preparing Enclosures

Preparation of Cells: A method of isolating keratinocytes, seeding solid support means with keratinocytes, and introducing cell-seeded support means into an enclosure is described in U.S. Pat. No. 5,972,332 (hereby incorporated by reference). Similar methodology is described for a transformed cell line expressing a transgene in U.S. patent application Ser. No. 09/323,188 filed May 27, 1999 and in U.S. Ser. No. 09/338,413, filed Feb. 11, 2000. Each referenced patent and application is incorporated herein in its entirety by reference. Virtually any other cell type that is mitotically competent in a cell culture medium could be selected by the skilled practitioner depending upon the specific purpose for which the subject article is to be used. Primary isolates may be seeded onto solid support means immediately, or passaged one or more times in cell culture before seeding. In the case of keratinocytes, the cell culture medium contains microgram per ml amounts of insulin, calcium (at concentrations lower than normal serum concentrations), microgram per ml amounts of a glucocorticoid, nanogram/ml amounts of epidermal growth factor, and nanogram/ml amounts of a saline extract of bovine pituitary.

Preparation of Solid Support Means: A solid support means with the following features is selected:

(i) Preferably, the solid support means is substantially incapable of escaping the enclosure. In this example, macroporous beads made of polyethylene and silica, sized to be large enough to stay inside an enclosure made of DELNET (P530 Natural, AET, Inc.) but otherwise small enough to maximize the surface area that a plurality of the beads provides for cell attachment and cell growth, were selected.

(ii) The solid support means preferably has a higher avidity for cells than for the selected enclosure material or the culture medium. In this case, the selected beads were treated with a solution of sodium hydroxide to effect this result, presumably by rendering the beads more negatively charged than the enclosure material or the culture medium.

(iii) A solid support means that is non-toxic to the cells (within the limits of the viability test described herein) is selected.

In the instant example, the selected solid support means, macroporous microcarrier beads made of polyethylene and silica, were autoclaved at 121° C. for 10 minutes in double distilled or microfiltered water. Following the autoclaving procedure, the beads were allowed to settle by gravity and were cooled. The supernatant water was then aspirated away from the beads. The beads were re-suspended in double distilled or microfiltered water and agitated by hand-swirling for a few seconds. The beads were again allowed to settle, the water aspirated and a final washing performed as above.

The beads were next treated with a solution of 0.1N NaOH, a preferred concentration, but not critical. Treatment continued at room temperature overnight. Thereafter the washing procedure set out above was repeated five times. The pH of the final suspension was measured with a conventional device at less than about 8. The beads were then transferred to sterile culture medium, at which point they are ready for seeding.

Preparation of the Enclosure: Variations in the procedure result in several embodiments of the final article.

(i) A sheet of DELNET, approximately 3×6 inches was folded once into a square shape and heat-sealed on two sides using a heat-sealing unit (IMPULSE manufactured by American International Electric Co.) to create a bag-like structure. Next, beads prepared as described above were introduced into the bag through the unsealed side. Approximately 1 ml of gravity-packed beads was introduced into the bag. The open side of the bag was then heat-sealed as above. The article was then immediately placed in culture medium, heat-sterilized at 121° C. for 30 minutes and stored in the culture medium for use in subsequent steps.

(ii) The bag prepared as described above, after equilibrating in culture medium at 37° C. for 4 days or more was inoculated with a primary culture of more than about one million keratinocytes per ml of gravity-packed beads and less than about two million keratinocytes per ml of gravity-packed beads. The keratinocytes were suspended in culture medium in a 3 cc syringe and injected through the DELNET material using an 18 ga. needle. The injected bag was then incubated, using conventional tissue culture apparatus, in approximately 1 ml of culture medium for 4 days at 37° C. under 95% $O_2$, 5% $CO_2$. The article was then ready for use. Alternatively, the bag and its contents may be frozen and used at a later time, after thawing.

(iii) A sheet of DELNET is fashioned into an open bag-like structure and sterilized. Cells pre-seeded onto sterile, equilibrated solid-support means are introduced into the bag and the bag is then sealed by means that are non-toxic to the cells. The sealed bag is then incubated as described above or for a time sufficient to permit growth of cells to a pre-determined number and then put to use or frozen for use at a later time.

(iv) A sheet of DELNET is fashioned into an open bag-like structure and sterilized. Cells in suspension and, separately, sterile, equilibrated solid-support means are introduced into the bag and the bag is then sealed by means that are non-toxic to cells. The sealed bag is then incubated as described above and put to use or frozen for use at a later time.

(v) Cells in suspension and, separately, sterilized solid-support means are introduced into a sterilized, entirely sealed enclosure. The enclosure is then incubated as described above and put to use or frozen for use at a later time. The frozen article is made useable by thawing and, using conventional tissue culture apparatus, incubating the article in culture medium for a sufficient time to permit seeding and growth of cells to a pre-determined number.

(vi) Cells in suspension are introduced into either an open bag or an entirely sealed bag and frozen. Separately, an equilibrated, sterile solid-support means is introduced into the same bag, sealed by an appropriate means if necessary, and frozen. At a later time, the bag is thawed and, using conventional tissue culture apparatus, incubated in culture medium for a sufficient time to permit seeding and growth of cells to a pre-determined number. The article is then ready for use.

(vii) An enclosure prepared as in (i) above is co-incubated with cells. However, the cells are not injected into the enclosure, but migrate into the enclosure. When the extent of cell immigration is sufficient to effect seeding of the solid support means, incubation of the enclosure and its contents continues, with or without replacement of the medium with cell-free medium, to permit growth of cells on the solid-support means to a pre-determined number. The Article is then put to use or frozen for use at a later time. The frozen article is made useable by thawing and, using conventional tissue culture apparatus, incubating the article in culture medium for a sufficient time to permit seeding and growth of cells to a pre-determined number.

Growing the Cells: Whether or not grown within or without the enclosure, cells were added to beads at a density of less than about two million cells per 1 ml of gravity-packed beads. Cells were grown in an incubator with slow agitation in a roller bottle. Cells attached to the beads within about 6 hours. The incubation medium was changed every other day. The temperature ranged between 36 and 38° C. and the medium was gassed with 5% $CO_2$–95% $O_2$.

Procedure for Assessing Viability of Cells in Enclosure:

Reagents:
1 µM calcein AM*+2 µM EthD-1* in D-PBS
1 µM calcein AM in D-PBS
2 µM EthD-1 in D-PBS
Dulbecco's Buffered Phosphate Saline (D-PBS)

Molecular Probes, LIVE/DEAD Viability/Cytotoxicity Kit (L-3224)

Solution Preparation for Experimental and Control Cell Samples:
Use within 24 hours of making Solution 1. Combination Solution (Live/Dead cells)
Add 20 µl EthD-1 to 10 ml D-PBS
Vortex to mix
Add 5 µcalcein to EthD-1 solution
Vortex to mix Solution 2. Calcein solution (live cells)
  Add 5 μl calcein to 10 ml D-PBS
  Vortex to mix Solution 3. EthD-1 solution (dead cells)
  Add 20 μl EthD-1 to 10 ml PBS
  Vortex to mix Experimental Sample Preparation:
Open a bag of cells/beads and place into a 35 mm Petri dish.
Aspirate the media.
Rinse cells/beads immediately with 3 ml of D-PBS.
Place aliquots of cells/beads into 4 Petri dishes for different treatments.
Aspirate the D-PBS.
Add enough of the combination solution (solution 1) to cover the cells/beads.
Incubate Petri dish at 37 degrees Celsius for 20 minutes.
View Petri dish under fluorescence microscope to confirm the cells have stained appropriately. (live cells: ex/em ~485/~530; dead cells: ex/em ~530/~645)
Randomly pick cells/beads from Petri dish and place into a 96 well plate.

Control Samples Preparation:

Plain Bead Controls:
Take plain prepared beads and place approximately 500 μl into 2 Petri dishes.
Aspirate soaking solution.
Rinse plain prepared beads with 3 ml of D-PBS.
Aspirate the D-PBS.
Add enough of Solution 2 to one Petri dish and Solution 3 to the remaining Petri dish to cover the beads.
Indubate Petri dishes at 37 degrees Celsius for 20 minutes.
Randomly pick beads and place into a 96 well plate.
Also take plain prepared beads (no solution treatments), rinsed in D-PBS and place into a 96 well plate.

Cells/bead Controls:
Take one of the cell/bead aliquot dishes and aspirate the D-PBS.
Add enough of the Calcein solution (solution 2) to cover the cells/beads.
Take another of the cell/bead aliquot dish and aspirate the D-PBS.
Add enough of the EthD-1 solution (solution 3) to cover the cells/beads.
Take a third cell/bead aliquot dish and aspirate the D-PBS.
Add enough D-PBS to cover the cells/beads.
Incubate all Petri dishes at 37 degrees Celsius for 20 minutes.
Randomly pick beads and place into a 96 well plate.

96 well plate set up:
Pipet 100 μl D-PBS into all wells, 2–3 beads per well
Add plain bead controls, cells/beads controls and experimental samples to multiple wells for analysis.

Microplate Reader Set Up:
Follow the instrument's procedure manual for setting up the reader for the appropriate filters and running the assay.
Calcein is excited using a fluorescein filter, 485±10 nm and an emission filter of 530±12.5nm.
Ethidium homodimer-1 (EthD-1) is excited with a rhodomine filter, 530±12.5 nm and an emission filter of 645±20 nm.

Fluorescence Measurements:
Run the assay first utilizing the Calcein set of filters then repeat the assay with the Ethidium filter set.
Background fluorescence (lain bead control) readings are subtracted from experimental sample wells.
Viability=ratio of live cells values (Calcein assay) to dead cells values (Ethidium assay).
Note: The minimum detectable number of cells per well is usually between 200 and 500.
The maximum usable number of cells per well is on the order of $10^6$ (Ref., LIVE/DEAD Viability Kit, Molecular Probes Inc., Information sheet).

EXAMPLE 6

Enclosures for Promoting Tumor Regression

This example describes enclosures and methods used to promote tumor regression. In particular, this example describes the use of enclosures containing cells transfected with human interleukin-1 (hIL-1) to reduce the size of tumors.

Mouse macrophage cells, RAW 264, were transfected with IL-1. The primer sequence for IL-1 was obtained from GeneBank. The primers employed were 5' ATGGCACCT-GTACGATCACT 3' (SEQ ID NO:1) and 5' TTCAGCA-CAGGACTCTCTGG 3' (SEQ ID NO: 2). cDNA fragments were generated by RT-PCR from human leukocytes. These fragments were cloned into the TA cloning vector (Invitrogen, Carlsbad, Calif.) and then subcloned into pcDNA4/TO expression Vector for the T-Rex system (Invitrogen, Carlsbad, Calif.). Orientation of the insert was confirmed by restriction enzyme digestion. DNA was prepared by using the Novagen UltraMobius Plasmid Isolation kit (Novagen, Madison, Wis.) to reduce endotoxin comtamination. The final DNA concentration for hIL-1 was 980 μg/ml. The LIPOFECTAMIN PLUS™ kit (Life Technologies, Rockwell, Md.) was use to perform the transfection. The plasmid was diluted in medium to 10 μg/ml then mixed with PLUS reagent and incubated. LIPOFECTAMINE was added to this mixture and incubated before being added to the RAW cells in culture.

The mouse macrophage cells RAW 264 were seeded onto CYTOLINE 1 macroporous microcarrier beads (Pharmacia Biotech, Uppsala, Sweden) at a concentration of $1\times10^6$ cells per 1 ml of microcarrier beads and allowed to attach for 2 days. The LIPOFECTAMIN hIL-1 mixture was combined with the RAW cells/beads and incubated. After 3 hours the transfected cell populated microcarrier beads were pipeted into fabric bag enclosure (0.5 ml beads per 23×25 cm bag) composed of DELNET material, and maintained in medium until application. The enclosure remained on the tumor only two days because the transfection was transient and was lost after 48 hour.

Twelve C57BLK/J mice had BL6 melanoma injected intramuscularly between the scapula with a tumor developing by 10 days. At that time the tumor was incompletely excised and the enclosure was placed over the remaining tumor and the wound closed over it using surgical staples. After 2 days the dressing was removed and the tumor was evaluated for size reduction or tumor recurrence over 21 days. A second group of mice (control) had their tumors incompletely excised, an enclosure with parental non-transfected RAW cells placed over the tumor and the wound closed. At 24 and 48 hours both groups of mice had blood and wound fluid collected for IL-1 determination by ELISA.

Figure 2:
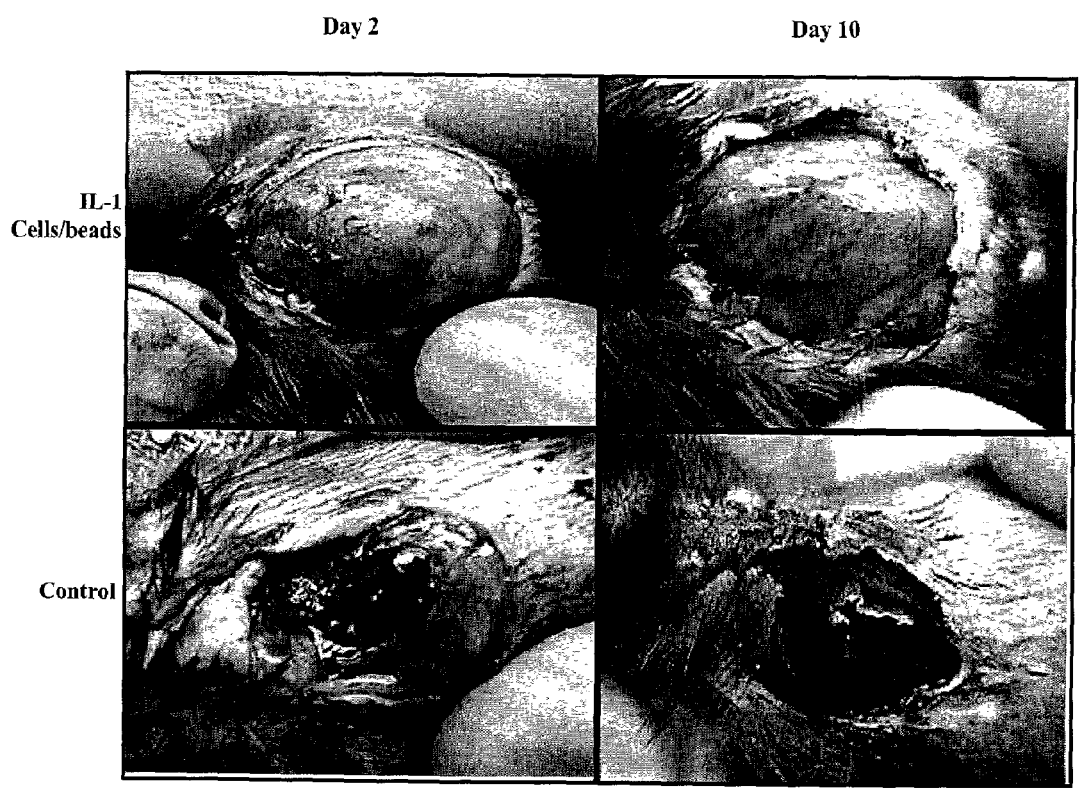
FIG. 2 illustrates the condition of a tumor in a mouse, compared to a control, after treatment with one embodiment of the cell-containing enclosures of the present invention.

Eight of the nine mice treated with hIL-1 transfected cells had no remaining tumor or had regression of the tumor. The three control mice treated with the non-transfected RAW 264 cells showed continued tumor growth. These results are present in FIG. 2. The top images in FIG. 2 are of a mouse that was treated with IL-1 transfected cell-containing enclosures, while the bottom images are of a control mouse. Images in the left column are from day 2, when the enclosure was removed from the mouse. The right column shows the tumor size at day 10. Note the recurrence of the melanoma in the control mouse at day 10. Also, nine mice lungs were evaluated for metastasis with none observed.

ELISA analysis of IL-1 from the serum samples detected none at either 24 or 48 hours. However, wound fluid from four randomly selected IL-1 treated mice averaged 991 pg/ml±508 at 24 hours and 74 pg/ml±37 at 48 hours. Two control mice chosen had no detectable IL-1. Medium from the unused IL-1 cells/beads flasks contained 25,431 pg/ml of IL-1 while the control cells/beads medium had no detectable IL-1. These results are presented in Table 15.

TABLE 15

ELISA Results of Individual Mice

| Mouse | 24 hrs (pg/ml) | 48 hrs (pg/ml) |
|---|---|---|
| IL-1 Treated | | |
| 1 | 244 | 71 |
| 2 | 740 | 176 |
| 3 | 495 | 49 |
| 4 | 2481 | 155 |
| Control Treated | | |
| 5 | <1.22 | <1.22 |
| 6 | <1.22 | <1.22 |
| Stock Cell Control | | |
| Medium IL-1 cell/bead flask | 25,431 | |
| Medium non-transfected cell/bead flask | <1.22 | |

EXAMPLE 7

Tumor Susceptibility Data

This example describes a tumor susceptibility assay. In particular, was performed to determine if melanoma growth onto the beads was prevented in murine macrophages that were transfected with the gene encoding for IL-1

In this series of experiments, BL16 tumors were grown in the soft tissue of the back of C57/BLK/J mice. The tumors were incompletely excised and bead bags were placed on the wound. The bead bags contained the raw 264 macrophages grown on beads with or without cells transfected with the gene that encode for IL-1. The beads were removed from the bag after 48 hrs and placed in a petri dish. The difference in the number of beads or bead clumps containing black pigment were counted without magnification. The number beads/bead clumps with black pigment were expressed as a percentage of the total of the number counted.

The data demonstrates that beads containing the raw 264 macrophages transfected with the gene encoding for IL-1 had only 8% (2/50) beads/bead clumps containing black melanoma pigment. Whereas, 68% (24/34) bead/bead clumps contained black pigment if the raw 264 macrophages were not transfected with the gene that encoded for IL-1. This data indicates, since macrophages transfected with the gene than encodes for the production IL-1 prevents melanoma growth on the bead/bead clumps in vitro, that the tumor that was the source of the melanoma cells would be susceptible to treatment with enclosures containing these cells.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, and molecular biology or related fields are intended to be within the scope of the following claims.

We claim:

1. A method for promoting tumor regression, comprising;
   a) providing;
      i) viable cells on solid support material, wherein said viable cells secrete recombinant human interleukin-1 beta protein,
      ii) an enclosure housing said solid support material, wherein said enclosure comprises mesh material, and
      iii) a subject with a tumor, wherein said tumor comprises metastatic melanoma cells, and,
   b) positioning said enclosure on said tumor of said subject such that regression of said tumor is promoted and such that metastasis of said melanoma cells to lung tissue of said subject is inhibited.

2. The method of claim 1, wherein said viable cells comprise an expression vector, wherein said expression vector comprises a nucleic acid sequence encoding said interleukin-1 beta protein.

3. The method of claim 1, wherein said solid support comprises beads.

4. The method of claim 1, wherein said mesh material comprises pores.

5. The method of claim 1, wherein said mesh material comprises pores ranging in size from about 1 micron to about 500 microns.

6. The method of claim 1, wherein said enclosure further comprises a removal component.

7. The method of claim 1, further comprising step c) removing said enclosure from said tumor after regression of said tumor is promoted.

8. The method of claim 1, wherein said tumor is a cancerous tumor.

9. The method of claim 8, wherein said cancerous tumor is a skin cancer tumor.

10. The method of claim 1, wherein said viable cells are human foreskin cells.

11. A method for promoting tumor regression, comprising;
    a) providing;
       i) viable cells on solid support material, wherein said viable cells secrete recombinant human interleukin1 beta, and wherein said viable cells do not secrete recombinant human interleukin1 alpha,
       ii) an enclosure housing said solid support material, wherein said enclosure comprises mesh material, and
       iii) a subject with a tumor, wherein said tumor comprises metastatic melanoma cells, and
    b) positioning said enclosure on said tumor of said subject such that regression of said tumor is promoted and such that metastasis of said melanoma cells to lung tissue of said subject is inhibited.

12. The method of claim 11, wherein said viable cells comprise an expression vector, wherein said expression vector comprises a nucleic acid sequence encoding said interleukin1 beta protein.

13. The method of claim 11, wherein said solid support comprises beads.

14. The method of claim 11, wherein said mesh material comprises pores.

15. The method of claim 11, wherein said mesh material comprises pores ranging in size from about 1 micron to about 500 microns.

16. The method of claim 11, wherein said enclosure further comprises a removal component.

17. The method of claim 11, further comprising step c) removing said enclosure from said tumor after regression of said tumor is promoted.

18. The method of claim 11, wherein said tumor is a cancerous tumor.

19. The method of claim 18, wherein said cancerous tumor is a skin cancer tumor.

20. The method of claim 11, wherein said viable cells are human foreskin cells.

* * * * *